United States Patent
Kawai et al.

(10) Patent No.: US 10,734,682 B2
(45) Date of Patent: Aug. 4, 2020

(54) ELECTROLYTIC SOLUTION

(71) Applicant: KABUSHIKI KAISHA TOYOTA JIDOSHOKKI, Kariya-Shi, Aichi-Ken (JP)

(72) Inventors: Tomoyuki Kawai, Kariya (JP); Yuki Hasegawa, Kariya (JP); Junichi Niwa, Kariya (JP); Hiroyuki Sasaki, Kariya (JP)

(73) Assignee: KABUSHIKI KAISHA TOYOTA JIDOSHOKKI, Kariya-shi, Aichi (JP)

( * ) Notice: Subject to any disclaimer, the term of this patent is extended or adjusted under 35 U.S.C. 154(b) by 132 days.

(21) Appl. No.: 15/555,617

(22) PCT Filed: Feb. 26, 2016

(86) PCT No.: PCT/JP2016/001064
§ 371 (c)(1),
(2) Date: Sep. 5, 2017

(87) PCT Pub. No.: WO2016/143294
PCT Pub. Date: Sep. 15, 2016

(65) Prior Publication Data
US 2018/0048024 A1 Feb. 15, 2018

(30) Foreign Application Priority Data
Mar. 10, 2015 (JP) .................. 2015-047043

(51) Int. Cl.
*H01M 10/0567* (2010.01)
*H01M 4/38* (2006.01)
(Continued)

(52) U.S. Cl.
CPC ......... *H01M 10/0567* (2013.01); *C07C 69/96* (2013.01); *H01G 11/06* (2013.01);
(Continued)

(58) Field of Classification Search
CPC ......... H01M 10/0567; H01M 10/0568; H01M 10/0569; H01M 10/0525; H01M 10/052;
(Continued)

(56) References Cited

U.S. PATENT DOCUMENTS 5,192,629 A 3/1993 Guyomard et al.
8,586,250 B2 11/2013 Iwaya
(Continued)

FOREIGN PATENT DOCUMENTS

CN 102498606 A 6/2012
CN 103250295 A 8/2013
(Continued)

OTHER PUBLICATIONS

Communication dated Sep. 13, 2018 in corresponding Korean patent application No. 10-2017-7024597.
(Continued)

*Primary Examiner* — Laura Weiner
(74) *Attorney, Agent, or Firm* — Sughrue Mion, PLLC

(57) ABSTRACT

An electrolytic solution containing
a specific organic solvent at a mole ratio of 1-8 relative to a metal salt,
the specific organic solvent being selected from a linear carbonate represented by general formula (1-1) below, an ester represented by general formula (1-2) below, and a phosphoric ester represented by general formula (1-3) below,
the metal salt being a metal salt whose cation is an alkali metal, an alkaline earth metal, or aluminum and whose anion has a chemical structure including two or three types of elements selected from boron, carbon, oxygen, a halogen, phosphorus, and arsenic, wherein $R^{10}OCOOR^{11}$ general formula (1-1)

$R^{12}COOR^{13}$ general formula (1-2)

$OP(OR^{14})(OR^{15})(OR^{16})$ general formula (1-3).

16 Claims, 6 Drawing Sheets

(51) Int. Cl.

| | | |
|---|---|---|
| *H01M 10/0568* | (2010.01) | |
| *H01M 10/0569* | (2010.01) | |
| *H01G 11/06* | (2013.01) | |
| *C07C 69/96* | (2006.01) | |
| *H01G 11/32* | (2013.01) | |
| *H01G 11/62* | (2013.01) | |
| *H01G 11/60* | (2013.01) | |
| *H01M 4/505* | (2010.01) | |
| *H01M 4/525* | (2010.01) | |
| *H01M 4/587* | (2010.01) | |
| *H01M 4/66* | (2006.01) | |
| *H01M 10/0525* | (2010.01) | |
| *H01M 10/052* | (2010.01) | |

(52) U.S. Cl.
CPC ............. *H01G 11/32* (2013.01); *H01G 11/60* (2013.01); *H01G 11/62* (2013.01); *H01M 4/386* (2013.01); *H01M 4/505* (2013.01); *H01M 4/525* (2013.01); *H01M 4/587* (2013.01); *H01M 4/661* (2013.01); *H01M 10/0525* (2013.01); *H01M 10/0568* (2013.01); *H01M 10/0569* (2013.01); *H01M 10/052* (2013.01); *H01M 2300/0025* (2013.01); *H01M 2300/0028* (2013.01); *Y02E 60/13* (2013.01)

(58) Field of Classification Search
CPC ...... H01M 4/525; H01M 4/505; H01M 4/587; H01M 4/661; H01M 4/386; H01M 2300/0028; H01M 2300/0025; Y02E 60/13
See application file for complete search history.

(56) References Cited

U.S. PATENT DOCUMENTS

| | | | |
|---|---|---|---|
| 9,093,712 | B2 | 7/2015 | Kato et al. |
| 9,754,726 | B2 | 9/2017 | Onagi et al. |
| 2012/0164542 | A1 | 6/2012 | Iwaya |
| 2012/0171576 | A1 | 7/2012 | Tsai et al. |
| 2013/0209817 | A1 | 8/2013 | Nii et al. |
| 2013/0209871 | A1 | 8/2013 | Kato et al. |
| 2013/0266847 | A1 | 10/2013 | Noguchi et al. |
| 2015/0287537 | A1 | 10/2015 | Onagi et al. |
| 2015/0318541 | A1 | 11/2015 | Kim et al. |

FOREIGN PATENT DOCUMENTS

| | | | |
|---|---|---|---|
| JP | 07505740 | A | 6/1995 |
| JP | 09-306538 | A | 11/1997 |
| JP | 11233140 | A | 8/1999 |
| JP | 2006114388 | A | 4/2006 |
| JP | 2012-038564 | A | 2/2012 |
| JP | 2012-142260 | A | 7/2012 |
| JP | 2013-004316 | A | 1/2013 |
| JP | 2013-137873 | A | 7/2013 |
| JP | 2013-145724 | A | 7/2013 |
| JP | 2013-149477 | A | 8/2013 |
| JP | 2014-112524 | A | 6/2014 |
| JP | 2014130718 | A | 7/2014 |
| JP | 2014241198 | A | 12/2014 |
| JP | 2015-088741 | A | 5/2015 |
| JP | 2015-133312 | A | 7/2015 |
| WO | 9321665 | A1 | 10/1993 |
| WO | 2014/073712 | A1 | 5/2014 |
| WO | 2014142457 | A1 | 9/2014 |
| WO | 2014200012 | A1 | 12/2014 |

OTHER PUBLICATIONS

Communication dated Jul. 31, 2018 from the Japanese Patent Office in counterpart Japanese application No. 2017-504850.

Yuki Nagano et al., "High LiPF6 concentration electrolyte for improved energy density of dual carbon battery", Dai 53 Kai Abstracts, Battery Symposium in Japan, The committee of Battery Technology, The Electrochemical Society of Japan, Nov. 13, 2012, p. 504.

Communication dated Feb. 3, 2019 issued by the State Intellectual Property Office of People's Republic of China in corresponding application No. 201680014737.6.

International Search Report of PCT/JP2016/001064 dated Apr. 5, 2016.

Communication dated Jan. 15, 2020 from the State Intellectual Property Office of the P.R.C. in counterpart application No. 201680014737.6.

Number of moles of organic solvent / number of moles of metal salt

Number of moles of organic solvent / number of moles of metal salt

ELECTROLYTIC SOLUTION

CROSS REFERENCE TO RELATED APPLICATIONS

This application is a National Stage of International Application No. PCT/JP2016/001064 filed Feb. 26, 2016, claiming priority based on Japanese Patent Application No. 2015-047043 filed Mar. 10, 2015, the contents of all of which are incorporated herein by reference in their entirety.

TECHNICAL FIELD

The present invention relates to an electrolytic solution to be used in power storage devices such as secondary batteries.

BACKGROUND ART

Generally, a power storage device such as a secondary battery includes, as main components, a positive electrode, a negative electrode, and an electrolytic solution. In the electrolytic solution, an appropriate electrolyte is added in an appropriate concentration range. For example, in an electrolytic solution of a lithium ion secondary battery, a lithium salt such as $LiClO_4$, $LiAsF_6$, $LiBF_4$, and $LiB(C_2O_4)_2$ is commonly added as an electrolyte, and the concentration of the lithium salt in the electrolytic solution is set at about 1 mol/L.

In an organic solvent to be used in an electrolytic solution, a cyclic carbonate such as ethylene carbonate or propylene carbonate is generally mixed by not less than about 30 volt, in order to suitably dissolve an electrolyte.

Actually, Patent Literature 1 discloses a lithium ion secondary battery using an electrolytic solution that uses a mixed organic solvent containing ethylene carbonate by 33 vol % and that contains $LiPF_6$ at a concentration of 1 mol/L. Furthermore, Patent Literature 2 discloses a lithium ion secondary battery using an electrolytic solution that uses a mixed organic solvent containing ethylene carbonate and propylene carbonate by 50 wt % and that contains $LiPF_6$ at a concentration of 1.1 mol/L.

In addition, for the purpose of improving performance of batteries, studies are actively conducted for various additives to be added to an electrolytic solution containing a lithium salt.

For example, the above described Patent Literature 2 describes an electrolytic solution obtained by adding a small amount of a specific additive to a mixture that uses a mixed organic solvent containing ethylene carbonate and propylene carbonate at 50 wt % and that contains $LiPF_6$ at a concentration of 1.1 mol/L. Patent Literature 2 discloses a lithium ion secondary battery using this electrolytic solution. Patent Literature 3 describes an electrolytic solution obtained by adding a small amount of a specific additive to a mixture containing $LiPF_6$ at a concentration of 1 mol/L, and discloses a lithium ion secondary battery using this electrolytic solution. Furthermore, Patent Literature 4 also describes an electrolytic solution obtained by adding a small amount of phenyl glycidyl ether to a mixture containing $LiPF_6$ at a concentration of 1 mol/L, and discloses a lithium ion secondary battery using this electrolytic solution.

CITATION LIST

Patent Literature

Patent Literature 1: JP2013149477(A)
Patent Literature 2: JP2012142260(A)
Patent Literature 3: JP2013145724(A)
Patent Literature 4: JP2013137873(A)

SUMMARY OF INVENTION

Technical Problem

As described in Patent Literature 1 to 4, conventionally, with respect to an electrolytic solution used in a lithium ion secondary battery, using a lithium salt at a concentration of about 1 mol/L was technical common knowledge. In addition, as described in Patent Literature 2 to 4, studies for improving electrolytic solutions have been generally conducted with a focus on additives, separately from the lithium salt.

Contrary to such conventional technical common knowledge, the present invention is focused on the relationship between a metal salt and a solvent in an electrolytic solution. An object of the present invention is to provide a new electrolytic solution containing a specific metal salt and a specific solvent at a specific proportion.

Solution to Problem

The present inventors have conducted thorough investigation with much trial and error, without being confined to conventional technical common knowledge. As a result, the present inventors have found that a metal salt is dissolved at a higher concentration than an ordinary concentration in an organic solvent having a specific chemical structure. On the basis of this finding, the present inventors have completed the present invention.

An electrolytic solution of the present invention contains a specific organic solvent at a mole ratio of 1-8 relative to a metal salt, the specific organic solvent being selected from a linear carbonate represented by general formula (1-1) below, an ester represented by general formula (1-2) below, and a phosphoric ester represented by general formula (1-3) below, the metal salt being a metal salt whose cation is an alkali metal, an alkaline earth metal, or aluminum and whose anion has a chemical structure including two or three types of elements selected from boron, carbon, oxygen, a halogen, phosphorus, and arsenic.

| | |
|---|---|
| $R^{10}OCOOR^{11}$ | general formula (1-1) |
| $R^{12}COOR^{13}$ | general formula (1-2) |
| $OP(OR^{14})(OR^{15})(OR^{16})$ | general formula (1-3) |

($R^{10}$, $R^{11}$, $R^{12}$, $R^{13}$, $R^{14}$, $R^{15}$, and $R^{16}$ are each independently selected from $C_nH_aF_bCl_cBr_dI_e$ that is a linear alkyl, or $C_mH_fF_gCl_hBr_iI_j$ that includes a cyclic alkyl in a chemical structure thereof. "n" is an integer not smaller than 1, "m" is an integer not smaller than 3, and "a", "b", "c", "d", "e", "f", "g", "h", "i", and "j" are each independently an integer not smaller than 0 and satisfy $2n+1=a+b+c+d+e$ and $2m=f+g+h+i+j$)

Advantageous Effects of Invention

The new electrolytic solution of the present invention is suitable as an electrolytic solution of power storage devices such as secondary batteries or the like.

DESCRIPTION OF EMBODIMENTS

Figure 1:
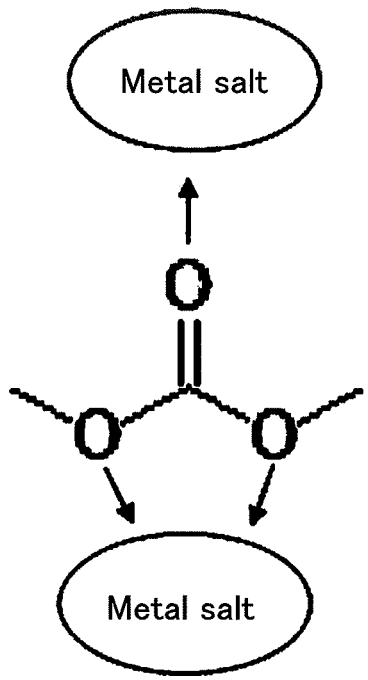
FIG. 1 is a model diagram illustrating interaction between one molecule of dimethyl carbonate and two molecules of a metal salt in an electrolytic solution.

The following describes embodiments of the present invention. Unless mentioned otherwise in particular, a numerical value range of "a to b (or, a-b)" described in the present specification includes, in the range thereof, a lower limit "a" and an upper limit "b". A numerical value range is formed by arbitrarily combining such upper limit values, lower limit values, and numerical values described in Examples. In addition, numerical values arbitrarily selected within a numerical value range may be used as upper limit and lower limit numerical values.

An electrolytic solution of the present invention contains a specific organic solvent at a mole ratio of 1-8 relative to a metal salt, the specific organic solvent being selected from a linear carbonate represented by general formula (1-1) below, an ester represented by general formula (1-2) below, and a phosphoric ester represented by general formula (1-3) below, the metal salt being a metal salt whose cation is an alkali metal, an alkaline earth metal, or aluminum and whose anion has a chemical structure including two or three types of elements selected from boron, carbon, oxygen, a halogen, phosphorus, and arsenic.

     general formula (1-1)

     general formula (1-2)

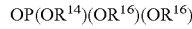     general formula (1-3)

($R^{10}$, $R^{11}$, $R^{12}$, $R^{13}$, $R^{14}$, $R^{15}$, and $R^{16}$ are each independently selected from $C_nH_aF_bCl_cBr_dI_e$ that is a linear alkyl, or $C_mH_fF_gCl_hBr_iI_j$ that includes a cyclic alkyl in a chemical structure thereof. "n" is an integer not smaller than 1, "m" is an integer not smaller than 3, and "a", "b", "c", "d.", "e", "f", "g", "h", "i", and "j" are each independently an integer not smaller than 0 and satisfy 2n+1=a+b+c+d+e and 2m=f+g+h+i+j.)

In a conventional electrolytic solution, a small amount of a metal salt is interspersed in a large number of solvent molecules. In this state, along with solvent that is coordinated with the metal salt, a large quantity of solvent that is not coordinated with the metal salt exists. In a conventional electrolytic solution, the solvent is contained at a mole ratio of about 10, relative to a metal salt.

In the electrolytic solution of the present invention, the specific organic solvent is contained at a mole ratio of 1-8 relative to the metal salt. In the electrolytic solution of the present invention, most of the specific organic solvent is considered to be coordinated with the metal salt (hereinafter, the state where the specific organic solvent and the metal salt are coordinated with each other is sometimes referred to as "cluster").

Each specific organic solvent has a chemical structure of O—C=O or O—P=O.

Here, for example, in a chemical structure O—C=O of a linear carbonate represented by general formula (1-1), unshared electron pairs of oxygen in O—C and unshared electron pairs of oxygen in C=O exist at opposite sides relative to the center of the molecule of the linear carbonate. In other words, the linear carbonate represented by general formula (1-1) has high electron density regions at opposite sides relative to the center of the molecule. This feature also applies to each ester represented by general formula (1-2) and each phosphoric ester represented by general formula (1-3).

The specific organic solvent having such a characteristic chemical structure of electron density regions is considered to realize a suitable coordinated state with the metal salt, thereby suitably allowing the metal salt to be dissolving therein.

Now, detail description is given using dimethyl carbonate serving as one mode of the linear carbonate represented by general formula (1-1). FIG. 1 shows a model diagram indicating interaction between one molecule of dimethyl carbonate and two molecules of a metal salt in an electrolytic solution. In dimethyl carbonate shown in FIG. 1, the unshared electron pairs of oxygen in C=O exist above the center of the molecule, and the unshared electron pairs of oxygen in O—C exist below the center of the molecule. Meanwhile, dimethyl carbonate is coordinated with one molecule of the metal salt by the unshared electron pairs of the upper oxygen, and is coordinated with another molecule of the metal salt by the unshared electron pairs of the lower oxygen. Here, as shown in FIG. 1, two molecules of the metal salt are away from each other while maintaining a stable coordinated state due to the chemical structure of dimethyl carbonate. Thus, in this state, these two molecules of the metal salt are difficult to come close to each other.

Figure 2:
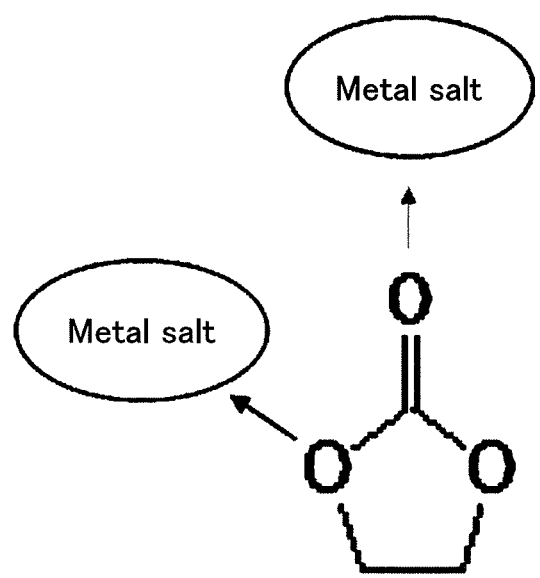
FIG. 2 is a model diagram illustrating interaction between one molecule of ethylene carbonate and two molecules of a metal salt in an electrolytic solution.

Meanwhile, for example, in a solvent that has only one unshared electron pair as in the case of acetonitrile, one molecule of the solvent is coordinated only with one molecule of the metal salt. Thus, another molecule of the metal salt easily comes close to the metal salt coordinated with the solvent. To look at a case of a solvent having a plurality of unshared electron pairs as in the case of ethylene carbonate, FIG. 2 shows a model diagram indicating interaction between one molecule of ethylene carbonate and two molecules of a metal salt in an electrolytic solution. A plurality of unshared electron pairs of ethylene carbonate exist substantially at the same side relative to the center of the molecule of ethylene carbonate. Thus, as shown in FIG. 2, the metal salt molecules coordinated with ethylene carbonate exist in the vicinity with each other, and thus, the metal salt molecules easily come close to each other.

Generally, a state where a solid solute is dissolved in a solvent is a state where the intermolecular force between solute molecules is cut and the solute molecules substantially uniformly exist in the solvent matrix. By the solvent solvating with the solute molecules, the state is suitably maintained. If the solute molecules come close to one another again, a solid which is an aggregate of the solute molecules is generated again, whereby the dissolved state is discontinued.

As shown in FIG. 1, the specific organic solvent prevents the metal salt as a solute from coming close to each other, due to the chemical structure of the specific organic solvent. Thus, the electrolytic solution of the present invention is considered to maintain a dissolved state of the metal salt even at a concentration higher than an ordinary concentration.

Meanwhile, as shown in FIG. 2, ethylene carbonate rather helps the metal salt as a solute to come close to each other. Thus, an electrolytic solution that contains a large amount of ethylene carbonate as the solvent and that contains a metal salt at a concentration higher than an ordinary concentration is considered to be difficult to maintain the dissolved state of the metal salt.

In general formula (1-1), general formula (1-2), or general formula (1-3), preferably, $R^{10}$, $R^{11}$, $R^{12}$, $R^{13}$, $R^{14}$, $R^{15}$, and $R^{16}$ are each independently selected from $C_nH_aF_b$ that is a linear alkyl, or $C_mH_fF_g$ that includes a cyclic alkyl in a chemical structure thereof. Here, "n" is an integer not smaller than 1, "m" is an integer not smaller than 3, and "a", "b", "f", and "g" are each independently an integer not smaller than 0 and satisfy $2n+1=a+b$ and $2m=f+g$.

"n" regarding general formula (1-1), general formula (1-2), or general formula (1-3) is preferably an integer from 1 to 6, more preferably an integer from 1 to 4, and particularly preferably an integer from 1 to 2. "m" is preferably an integer from 3 to 8, more preferably an integer from 4 to 7, and particularly preferably an integer from 5 to 6.

As the specific organic solvent, a linear carbonate represented by general formula (1-1) is preferable.

As the linear carbonate represented by general formula (1-1), dimethyl carbonate (hereinafter, sometimes referred to as "DMC"), diethyl carbonate (hereinafter, sometimes referred to as "DEC"), ethyl methyl carbonate (hereinafter, sometimes referred to as "EMC"), fluoromethyl methyl carbonate, difluoromethyl methyl carbonate, trifluoromethyl methyl carbonate, bis(fluoromethyl)carbonate, bis(difluoromethyl)carbonate, bis(trifluoromethyl)carbonate, fluoromethyl difluoromethyl carbonate, fluoromethyl trifluoromethyl carbonate, difluoromethyl trifluoromethyl carbonate, 2-fluoroethyl methyl carbonate, 2,2-difluoroethyl methyl carbonate, 2,2,2-trifluoroethyl methyl carbonate, pentafluoroethyl methyl carbonate, ethyl trifluoromethyl carbonate, fluoroethyl ethylcarbonate, trifluoroethyl ethylcarbonate, and bis(2,2,2-trifluoroethyl) carbonate are particularly preferable.

As the ester represented by general formula (1-2), methyl acetate, ethyl acetate, propyl acetate, butyl acetate, methyl propionate, ethyl propionate, methyl fluoroacetate, ethyl fluoroacetate, methyl difluoroacetate, ethyl difluoroacetate, methyl trifluoroacetate, ethyl trifluoroacetate, 2-fluoroethyl acetate, 2,2-difluoroethyl acetate, 2,2,2-trifluoroethyl acetate, 2-fluoroethyl fluoroacetate, 2,2-difluoroethyl fluoroacetate, 2,2,2-trifluoroethyl fluoroacetate, 2-fluoroethyl difluoroacetate, 2,2-difluoroethyl difluoroacetate, 2,2,2-trifluoroethyl difluoroacetate, 2-fluoroethyl trifluoroacetate, 2,2-difluoroethyl trifluoroacetate, 2,2,2-trifluoroethyl trifluoroacetate, methyl fluoropropionate, ethyl fluoropropionate, methyl difluoropropionate, ethyl difluoropropionate, methyl trifluoropropionate, ethyl trifluoropropionate, methyl tetrafluoropropionate, ethyl tetrafluoropropionate, methyl pentafluoropropionate, ethyl pentafluoropropionate, 2-fluoroethyl propionate, 2,2-difluoroethyl propionate, 2,2,2-trifluoroethyl propionate, 2-fluoroethyl fluoropropionate, 2,2-difluoroethyl fluoropropionate, 2,2,2-trifluoroethyl fluoropropionate, 2-fluoroethyl difluoropropionate, 2,2-difluoroethyl difluoropropionate, 2,2,2-trifluoroethyl difluoropropionate, 2-fluoroethyl trifluoropropionate, 2,2-difluoroethyl trifluoropropionate, 2,2,2-trifluoroethyl trifluoropropionate, 2-fluoroethyl tetrafluoropropionate, 2,2-difluoroethyl tetrafluoropropionate, 2,2,2-trifluoroethyl tetrafluoropropionate, 2-fluoroethyl pentafluoropropionate, 2,2-difluoroethyl pentafluoropropionate, and 2,2,2-trifluoroethyl pentafluoropropionate are particularly preferable.

As the phosphoric ester represented by general formula (1-3), trimethyl phosphate, ethyl dimethyl phosphate, diethyl methyl phosphate, triethyl phosphate, 2-fluoroethyl dimethyl phosphate, 2,2-difluoroethyl dimethyl phosphate, 2,2,2-trifluoroethyl dimethyl phosphate, 2-fluoroethyl diethyl phosphate, 2,2-difluoroethyl diethyl phosphate, 2,2,2-trifluoroethyl diethyl phosphate, bis(2-fluoroethyl) methyl phosphate, bis(2,2-difluoroethyl) methyl phosphate, bis(2,2,2-trifluoroethyl) methyl phosphate, bis(2-fluoroethyl) ethyl phosphate, bis(2,2-difluoroethyl) ethyl phosphate, bis(2,2,2-trifluoroethyl) ethyl phosphate, tris(2-fluoroethyl) phosphate, tris(2,2-difluoroethyl) phosphate, and tris(2,2,2-trifluoroethyl) phosphate are particularly preferable.

The linear carbonate represented by general formula (1-1), the ester represented by general formula (1-2), and the phosphoric ester represented by general formula (1-3) described above may be each singly used in the electrolytic solution, or may be used in combination of a plurality of these.

Examples of a cation of the metal salt in the electrolytic solution of the present invention include alkali metals such as lithium, sodium, and potassium, alkaline earth metals such as beryllium, magnesium, calcium, strontium, and barium, and aluminum. The cation of the metal salt is preferably a metal ion identical to a charge carrier of the battery in which the electrolytic solution is used. For example, when the electrolytic solution of the present invention is to be used as an electrolytic solution for lithium ion secondary batteries, the cation of the metal salt is preferably lithium.

The chemical structure of the anion of the metal salt is preferably any one of $XO_4$, $AsX_6$, $PX_6$, $BX_4$, and $B(C_2O_4)_2$ (each X independently means a halogen or CN). X is selected from F, Cl, Br, I, and CN as appropriate. Suitable examples of $XO_4$, $AsX_6$, $PX_6$, and $BX_4$ include $ClO_4$, $AsF_6$, $PF_6$, $BF_4$, and $BF_y(CN)_z$ (y is an integer from 0 to 3, z is an integer from 1 to 4, and y and z satisfy $y+z=4$).

As the metal salt of the present invention, one that is obtained by combining appropriate numbers of a cation and an anion described above may be used. As the metal salt in the electrolytic solution of the present invention, a single type may be used, or a combination of a plurality of types may be used.

The electrolytic solution of the present invention may include another electrolyte usable in an electrolytic solution for power storage devices, other than the metal salt described above. In the electrolytic solution of the present invention, the metal salt is contained by preferably not less than 50 mass %, more preferably not less than 70 mass %, and further preferably not less than 90 mass %, relative to the entire electrolyte contained in the electrolytic solution of the present invention. In addition, in the electrolytic solution of the present invention, the metal salt is contained by preferably not less than 50 mole %, more preferably not less than 70 mole %, and further preferably not less than 90 mole %, relative to the entire electrolyte contained in the electrolytic solution of the present invention.

In the electrolytic solution of the present invention, the specific organic solvent is contained at a mole ratio of 1-8 relative to the metal salt. If the mole ratio is less than 1, the density and the viscosity of the electrolytic solution become too high, thus causing a risk of significant decrease in the ionic conductivity of the electrolytic solution. If the mole ratio exceeds 8, the number of ions involved in ionic conduction decreases. Accordingly, a risk of decrease in the ionic conductivity of the electrolytic solution is caused and a risk is caused that, when charging and discharging is performed at a large current, the amount of Li ion supply to the electrode via the electrolytic solution becomes short, resulting in increase in the resistance (diffusion resistance). In addition, risks of worsening of solidification at low temperature and worsening of corrosiveness of an aluminum current collector at the time of high potential drive of a power storage device equipped with the electrolytic solution exist. Examples of the range of the mole ratio in the electrolytic solution of the present invention include 1-5, 1-4, 1-3, 1-6, 2-6, 2-5, 2-4, 2-3, 3-5, and 3-4. In conventional electrolytic solutions, the mole ratio of the organic solvent to the metal salt is about 10.

The suitable range of the mole ratio above varies depending on the type of the metal salt. For example, from the viewpoint of ionic conductivity, when the chemical structure of the anion of the metal salt is $PX_6$, the mole ratio is preferably in a range of 4 to 8, more preferably in a range of 5 to 7, and further preferably in a range of 5 to 6. When the chemical structure of the anion of the metal salt is $BX_4$, the mole ratio is preferably in a range of 2 to 6, more preferably in a range of 3 to 5, and further preferably in a range of 3 to 4.

In the vibrational spectroscopy spectrum of the electrolytic solution of the present invention, if, with respect to the intensity of a peak derived from the specific organic solvent, the intensity of an original peak of the specific organic solvent is defined as Io and the intensity of a peak resulting from shifting of the original peak of the specific organic solvent (hereinafter, sometimes referred to as "shift peak") defined as Is, Is>0.8×Io is satisfied in some cases. Suitable electrolytic solutions among the electrolytic solutions of the present invention satisfy Is>Io.

Here, the "original peak of the specific organic solvent" means the peak observed at a peak position (wave number) when vibrational spectroscopy measurement is performed only on the specific organic solvent. The value of the intensity Io of the original peak of the organic solvent and the value of the intensity Is of the shift peak each represent the height or the area from a baseline of each peak in the vibrational spectroscopy spectrum.

As described above, in the electrolytic solution of the present invention, most of the specific organic solvent is considered as forming a cluster by being coordinated with the metal salt.

The specific organic solvent that is forming a cluster and the specific organic solvent that is not involved in formation of the cluster have different environments in which the respective specific organic solvents exist. Thus, in the vibrational spectroscopy measurement, a peak derived from the specific organic solvent that is forming the cluster is observed as being shifted toward the high wave number side or the low wave number side relative to the wave number observed at a peak (i.e., original peak of the specific organic solvent) derived from the specific organic solvent that is not involved in the formation of the cluster.

In the vibrational spectroscopy spectrum of the electrolytic solution of the present invention, when a plurality of the shift peaks exist, the relationship between Is and Io may be determined on the basis of a peak enabling easiest determination of the relationship. In addition, when a plurality of types of the specific organic solvent are used in the electrolytic solution of the present invention, an organic solvent (having most significant difference between Is and Io) that enables easiest determination of the relationship between Is and Io is selected, and the relationship between Is and Io may be determined on the basis of the peak intensity thereof. In addition, when the peak shift amount is small and peaks before and after the shift overlap each other to give an appearance like a smooth mountain, the relationship between Is and Io may be determined by performing peak resolution with known means.

Examples of the vibrational spectroscopy spectrum include an IR spectrum or a Raman spectrum. Examples of measuring methods of IR spectrum include transmission measuring methods such as Nujol mull method and liquid film method, and reflection measuring methods such as ATR method. Regarding which of the IR spectrum or the Raman spectrum is to be selected, a spectrum enabling easy determination of the relationship between Is and Io may be selected as the vibrational spectroscopy spectrum of the electrolytic solution of the present invention. The vibrational spectroscopy measurement is preferably performed at a condition where the influence of moisture in the atmosphere can be reduced or ignored. For example, the IR measurement is preferably performed under a low humidity or zero humidity condition such as in a dry room or a glovebox, or the Raman measurement is preferably performed in a state where the electrolytic solution is kept inside a sealed container.

Regarding a wave number of a specific organic solvent and the attribution thereof, known data may be referenced. Examples of the reference include "Raman spectrometry" Spectroscopical Society of Japan measurement method series 17, Hiroo Hamaguchi and Akiko Hirakawa, Japan Scientific Societies Press, pages 231 to 249. In addition, a wave number of a specific organic solvent considered to be useful in calculation of Io and Is, and a shift in the wave number when the specific organic solvent and the metal salt are coordinated with each other are predicted from a calculation using a computer. For example, the calculation may be performed by using Gaussian09 (Registered trademark, Gaussian, Inc.), and setting the density functional to B3LYP and the basis function to 6-311G++(d, p). A person skilled in the art can calculate Io and Is by selecting a peak of the specific organic solvent with reference to known data and a calculation result from a computer.

In a vibrational spectroscopy spectrum chart obtained by subjecting the electrolytic solution of the present invention to vibrational spectroscopy measurement, a peak derived from the chemical structure of the anion of the metal salt is sometimes observed to shift to the low wave number side or the high wave number side. Examples of the vibrational spectroscopy spectrum include IR spectrum or Raman spectrum.

Since the electrolytic solution of the present invention contains the metal salt at a high concentration, the cation and the anion forming the metal salt are speculated to strongly interact with each other, whereby the metal salt is mostly in a CIP (contact ion pairs) state or an AGG (aggregate) state. Such a change in the state is observed as a shift of a peak derived from the chemical structure of the anion of the metal salt in the vibrational spectroscopy spectrum chart.

In the electrolytic solution of the present invention, the existence proportion of the metal salt is considered to be high compared to that in conventional electrolytic solutions. Then, in the electrolytic solution of the present invention, the environment in which the metal salt and the organic solvent exist is considered to be different from that in conventional electrolytic solutions. Therefore, in a power storage device such as a secondary battery using the electrolytic solution of the present invention, improvement in metal ion transportation rate in the electrolytic solution, improvement in reaction rate at the interface between an electrode and the electrolytic solution, mitigation of uneven distribution of metal salt concentration of the electrolytic solution caused when the secondary battery undergoes high-rate charging and discharging, improvement in liquid retaining property of the electrolytic solution at an electrode interface, suppression of a so-called liquid run-out state of lacking the electrolytic solution at an electrode interface, increase in the capacity of an electrical double layer, and the like are expected. Furthermore, in the electrolytic solution of the present invention, the vapor pressure of the organic solvent contained in the electrolytic solution decreases. As a result, volatilization of the organic solvent from the electrolytic solution of the present invention is reduced.

The electrolytic solution of the present invention contains a cation of the metal salt at a high concentration. Thus, the distance between adjacent cations is extremely small within the electrolytic solution of the present invention. When a cation such as a lithium ion moves between a positive electrode and a negative electrode during charging and discharging of the secondary battery, a cation located closest to an electrode that is a movement destination is firstly supplied to the electrode. Then, to the place where the supplied cation had been located, another cation adjacent to the cation moves. Thus, in the electrolytic solution of the present invention, a domino toppling-like phenomenon is predicted to be occurring in which adjacent cations sequentially change their positions one by one toward an electrode that is a supply target. Because of that, the distance for which a cation moves in the electrolytic solution during charging and discharging is considered to be short, and movement speed of the cation is considered to be high, accordingly. Because of this reason, the electrolytic solution of the present invention is considered to have ion conductivity even at a high viscosity.

Without departing from the gist of the present invention, a known solvent may be added to the electrolytic solution of the present invention.

Specific examples of such other solvent include: nitriles such as acetonitrile (hereinafter, sometimes referred to as "AN"), propionitrile, acrylonitrile, and malononitrile; ethers such as 1,2-dimethoxyethane (hereinafter, sometimes referred to as "DME"), 1,2-diethoxyethane, tetrahydrofuran, 1,2-dioxane, 1,3-dioxane, 1,4-dioxane, 2,2-dimethyl-1,3-dioxolane, 2-methyltetrahydropyran, 2-methyltetrahydrofuran, and crown ethers; cyclic carbonates such as ethylene carbonate, and propylene carbonate; amides such as formamide, N,N-dimethylformamide (hereinafter, sometimes referred to as "DMF"), N,N-dimethylacetamide, and N-methylpyrrolidone; isocyanates such as isopropyl isocyanate, n-propylisocyanate, and chloromethyl isocyanate; esters such as methyl formate, ethyl formate, vinyl acetate, methyl acrylate, and methyl methacrylate; epoxies such as glycidyl methyl ether, epoxy butane, and 2-ethyloxirane; oxazoles such as oxazole, 2-ethyloxazole, oxazoline, and 2-methyl-2-oxazoline; ketones such as acetone, methyl ethyl ketone, and methyl isobutyl ketone; acid anhydrides such as acetic anhydride and propionic anhydride; sulfones such as dimethyl sulfone and sulfolane; sulfoxides such as dimethyl sulfoxide; nitros such as 1-nitropropane and 2-nitropropane; furans such as furan and furfural; cyclic esters such as γ-butyrolactone, γ-valerolactone, and δ-valerolactone; aromatic heterocycles such as thiophene and pyridine; and heterocycles such as tetrahydro-4-pyrone, 1-methylpyrrolidine, and N-methylmorpholine.

In the electrolytic solution of the present invention, the linear carbonate represented by general formula (1-1), the ester represented by general formula (1-2), or the phosphoric ester represented by general formula (1-3) is preferably contained by, for example, not less than 70 vol %, not less than 80 vol %, not less than 90 vol %, or not less than 95 vol %, relative to the entire solvent contained in the electrolytic solution of the present invention. In addition, in the electrolytic solution of the present invention, the linear carbonate represented by general formula (1-1), the ester represented by general formula (1-2), or the phosphoric ester represented by general formula (1-3) is preferably contained by, for example, not less than 70 mole %, not less than 80 mole %, not less than 90 mole %, or not less than 95 mole %, relative to the entire solvent contained in the electrolytic solution of the present invention.

When the organic solvent formed from a hydrocarbon is added to the electrolytic solution of the present invention, an effect that the viscosity of the electrolytic solution is reduced is expected.

Specific examples of the organic solvent formed from the above hydrocarbon include benzene, toluene, ethyl benzene, o-xylene, m-xylene, p-xylene, 1-methylnaphthalene, hexane, heptane, and cyclohexane.

In addition, to the electrolytic solution of the present invention, a fire-resistant solvent may be added. By adding the fire-resistant solvent to the electrolytic solution of the present invention, safety of the electrolytic solution of the present invention is further enhanced. Examples of the fire-resistant solvent include halogen-based solvents such as carbon tetrachloride, tetrachloroethane, and hydrofluoroether.

When the electrolytic solution of the present invention is mixed with a polymer or an inorganic filler to form a mixture, the mixture enables containment of the electrolytic solution to provide a pseudo solid electrolyte. By using the pseudo solid electrolyte as an electrolytic solution of a battery, leakage of the electrolytic solution in the battery is suppressed.

As the polymer, a polymer used in batteries such as lithium ion secondary batteries and a general chemically cross-linked polymer are used. In particular, a polymer capable of turning into a gel by absorbing an electrolytic solution, such as polyvinylidene fluoride and polyhexafluoropropylene, and one obtained by introducing an ion conductive group to a polymer such as polyethylene oxide are suitable.

Specific examples of the polymer include polymethyl acrylate, polymethyl methacrylate, polyethylene oxide, polypropylene oxide, polyacrylonitrile, polyvinylidene fluoride, polyethylene glycol dimethacrylate, polyethylene glycol acrylate, polyglycidol, polytetrafluoroethylene, polyhexafluoropropylene, polysiloxane, polyvinyl acetate, polyvinyl alcohol, polyacrylic acid, polymethacrylic acid, polyitaconic acid, polyfumaric acid, polycrotonic acid, polyangelic acid, polycarboxylic acid such as carboxymethyl cellulose, styrene-butadiene rubbers, nitrile-butadiene rubbers, polystyrene, polycarbonate, unsaturated polyester obtained through copolymerization of maleic anhydride and glycols, polyethylene oxide derivatives having a substituent group, and a copolymer of vinylidene fluoride and hexafluoropropylene. In addition, as the polymer, a copolymer obtained through copolymerization of two or more types of monomers forming the above described specific polymers may be selected.

Polysaccharides are also suitable as the polymer. Specific examples of the polysaccharides include glycogen, cellulose, chitin, agarose, carrageenan, heparin, hyaluronic acid, pectin, amylopectin, xyloglucan, and amylose. In addition, materials containing these polysaccharides may be used as the polymer, and examples of the materials include agar containing polysaccharides such as agarose.

As the inorganic filler, inorganic ceramics such as oxides and nitrides are preferable.

Inorganic ceramics have hydrophilic and hydrophobic functional groups on their surfaces. Thus, a conductive passage may form within the inorganic ceramics when the functional groups attract the electrolytic solution. Furthermore, the inorganic ceramics dispersed in the electrolytic solution form a network among the inorganic ceramics themselves due to the functional groups, and may serve as containment of the electrolytic solution. With such a function by the inorganic ceramics, leakage of the electrolytic solution in the battery is further suitably suppressed. In order to have the inorganic ceramics suitably exert the function described above, the inorganic ceramics having a particle shape are preferable, and those whose particle sizes are nano level are particularly preferable.

Examples of the types of the inorganic ceramics include common alumina, silica, titania, zirconia, and lithium phosphate. In addition, inorganic ceramics that have lithium conductivity themselves are preferable, and specific examples thereof include $Li_3N$, $LiI$, $LiI-Li_3N-LiOH$, $LiI-Li_2S-P_2O_5$, $LiI-Li_2S-P_2S_5$, $LiI-Li_2S-B_2S_3$, $Li_2O-B_2S_3$, $Li_2O-V_2O_3-SiO_2$, $Li_2O-B_2O_3-P_2O_5$, $Li_2O-B_2O_3-ZnO$, $Li_2O-Al_2O_3-TiO_2-SiO_2-P_2O_5$, $LiTi_2(PO_4)_3$, $Li-\beta Al_2O_3$, and $LiTaO_3$.

Glass ceramics may be used as the inorganic filler. Since glass ceramics enables containment of ionic liquids, the same effect is expected for the electrolytic solution of the present invention. Examples of the glass ceramics include compounds represented by $xLi_2S-(1-x)P_2S_5$, and those in which one portion of S in the compound is substituted with another element and those in which one portion of P in the compound is substituted with germanium.

Without departing from the gist of the present invention, a known additive may be added to the electrolytic solution of the present invention. Examples of such a known additive include: cyclic carbonates including an unsaturated bond represented by vinylene carbonate (VC), vinylethylene carbonate (VEC), methyl vinylene carbonate (MVC), and ethyl vinylene carbonate (EVC); carbonate compounds represented by fluoro ethylene carbonate, trifluoro propylene carbonate, phenylethylene carbonate, and erythritane carbonate; carboxylic anhydrides represented by succinic anhydride, glutaric anhydride, maleic anhydride, citraconic anhydride, glutaconic anhydride, itaconic anhydride, diglycolic anhydride, cyclohexanedicarboxylic anhydride, cyclopentanetetracarboxylic dianhydride, and phenyl succinic anhydride; lactones represented by γ-butyrolactone, γ-valerolactone, γ-caprolactone, δ-valerolactone, δ-caprolactone, and ε-caprolactone; cyclic ethers represented by 1,4-dioxane; sulfur-containing compounds represented by ethylene sulfite, 1,3-propanesultone, 1,4-butanesultone, methyl methanesulfonate, busulfan, sulfolane, sulfolene, dimethylsulfone, and tetramethylthiuram monosulfide; nitrogen-containing compounds represented by 1-methyl-2-pyrrolidinone, 1-methyl-2-piperidone, 3-methyl-2-oxazolidinone, 1,3-dimethyl-2-imidazolidinone, and N-methylsuccinimide; phosphates represented by monofluorophosphate and difluorophosphate; saturated hydrocarbon compounds represented by heptane, octane, and cycloheptane; and unsaturated hydrocarbon compounds represented by biphenyl, alkyl biphenyl, terphenyl, partially hydrogenated terphenyl, cyclohexylbenzene, t-butylbenzene, t-amyl benzene, diphenyl ether, and dibenzofuran.

A method for producing the electrolytic solution of the present invention is described. Since the electrolytic solution of the present invention contains a larger amount of the metal salt than conventional electrolytic solutions, a production method in which the specific organic solvent is added to a solid (powder) metal salt causes an aggregate to be generated, and producing an electrolytic solution in a solution state is difficult in some cases. Thus, in the method for producing the electrolytic solution of the present invention, the metal salt is preferably gradually added to the specific organic solvent while a solution state of the electrolytic solution is maintained during production.

Alternatively, the electrolytic solution of the present invention may be produced by mixing in advance predetermined amounts of the specific organic solvent and the metal salt together, and then, by completing dissolution of the metal salt under supersonic vibration, high-speed stirring, or strong shear-force stirring, and/or heating in a refluxing condition of the specific organic solvent.

The electrolytic solution of the present invention described above is suitably used as the electrolytic solution for power storage devices such as batteries. In particular, the electrolytic solution of the present invention is preferably used as the electrolytic solution for capacitors and secondary batteries, and is particularly preferably used as the electrolytic solution for lithium ion secondary batteries, electrical double layer capacitors, and lithium ion capacitors. Hereinafter, a secondary battery provided with the electrolytic solution of the present invention is sometimes referred to as "secondary battery of the present invention", a lithium ion secondary battery provided with the electrolytic solution of the present invention is sometimes referred to as "lithium ion secondary battery of the present invention", and a capacitor provided with the electrolytic solution of the present invention is sometimes referred to as "capacitor of the present invention".

In the following, the lithium ion secondary battery of the present invention provided with the electrolytic solution of the present invention is described.

The lithium ion secondary battery of the present invention includes: a negative electrode having a negative electrode active material capable of occluding and releasing lithium ions; a positive electrode having a positive electrode active material capable of occluding and releasing lithium ions; and the electrolytic solution of the present invention using a lithium salt as the metal salt.

As the negative electrode active material, a material capable of occluding and releasing lithium ions is used. Thus, the material is not limited in particular as long as the material is an elemental substance, an alloy, or a compound capable of occluding and releasing lithium ions. For example, an elemental substance from among Li, group 14 elements such as carbon, silicon, germanium, and tin, group 13 elements such as aluminum and indium, group 12 elements such as zinc and cadmium, group 15 elements such as antimony and bismuth, alkaline earth metals such as magnesium and calcium, and group 11 elements such as silver and gold may be used as the negative electrode active material. When silicon or the like is used as the negative electrode active material, a high capacity active material is obtained since a single silicon atom reacts with multiple lithium atoms. However, a risk of occurrence of a problem regarding a significant expansion and contraction of volume associated with occlusion and release of lithium exists. Thus, in order to mitigate the risk, a substance obtained by combining an elemental substance of silicon or the like with another element such as a transition metal is suitably used as the negative electrode active material. Specific examples of the alloy or the compound include tin-based materials such as Ag—Sn alloys, Cu—Sn alloys, and Co—Sn alloys, carbon-based materials such as various graphites, silicon-based materials such as $SiO_x$ ($0.3 \leq x \leq 1.6$) that undergoes disproportionation into the elemental substance silicon and silicon dioxide, and a complex obtained by combining a carbon-based material with elemental substance silicon or a silicon-based material. In addition, as the negative electrode active material, an oxide such as $Nb_2O_5$, $TiO_2$, $Li_4Ti_5O_{12}$, $WO_2$, $MoO_2$, and $Fe_2O_3$, or a nitride represented by $Li_{3-x}M_xN$ (M=Co, Ni, Cu) may be used. With regard to the negative electrode active material, one or more types described above may be used.

A more specific example of the negative electrode active material is a graphite whose G/D ratio is not lower than 3.5. The G/D ratio is the ratio of G-band and D-band peaks in a Raman spectrum. In the Raman spectrum of graphite, G-band is observed near 1590 $cm^{-1}$ and D-band is observed near 1350 $cm^{-1}$, as peaks, respectively. G-band is derived from a graphite structure and D-band is derived from defects. Thus, having a higher G/D ratio, which is the ratio of G-band and D-band, means the graphite has higher crystallinity with fewer defects. Hereinafter, a graphite whose G/D ratio is not lower than 3.5 is sometimes referred to as a high-crystallinity graphite, and a graphite whose G/D ratio is lower than 3.5 is sometimes referred to as a low-crystallinity graphite.

As such a high-crystallinity graphite, both natural graphites and artificial graphites may be used. When a classification method based on shape is used, flake-like graphites, spheroidal graphites, block-like graphite, earthy graphites, and the like may be used. In addition, coated graphites obtained by coating the surface of a graphite with a carbon material or the like may also be used.

Examples of specific negative electrode active materials include carbon materials whose crystallite size is not larger than 20 nm, and preferably not larger than 5 nm. A larger crystallite size means that the carbon material has atoms arranged periodically and precisely in accordance with a certain rule. On the other hand, a carbon material whose crystallite size is not larger than 20 nm is considered to have atoms being in a state of poor periodicity and poor preciseness in arrangement. For example, when the carbon material is a graphite, the crystallite size becomes not larger than 20 nm when the size of a graphite crystal is not larger than 20 nm or when atoms forming the graphite are arranged irregularly due to distortion, defects, and impurities, etc.

Representative carbon materials whose crystallite size is not larger than 20 nm include hardly graphitizable carbon which is so-called hard carbon, and easily graphitizable carbon which is so-called soft carbon.

In order to measure the crystallite size of the carbon material, an X-ray diffraction method using CuK-alpha radiation as an X-ray source may be used. With the X-ray diffraction method, the crystallite size is calculated using the following Scherrer's equation on the basis of a half width of a diffraction peak detected at a diffraction angle of $2\theta=20$ degrees to 30 degrees and the diffraction angle.

$$L = 0.94 \lambda / (\beta \cos \theta)$$

where
L: crystallite size
$\lambda$: incident X-ray wavelength (1.54 angstrom)
$\beta$: half width of peak (radian)
$\theta$: diffraction angle.

Specific examples of the negative electrode active material include materials containing silicon. A more specific example is $SiO_x$ ($0.3 \leq x \leq 1.6$) disproportionated into two phases of Si phase and silicon oxide phase. The Si phase in $SiO_x$ is capable of occluding and releasing lithium ions, and changes in volume associated with charging and discharging of the secondary battery. The silicon oxide phase changes less in volume associated with charging and discharging when compared to the Si phase. Thus, $SiO_x$ as the negative electrode active material achieves higher capacity because of the Si phase, and when included in the silicon oxide phase, suppresses change in volume of the entirety of the negative electrode active material. When "x" becomes smaller than a lower limit value, cycle characteristics of the secondary battery deteriorate since the change in volume during charging and discharging becomes too large due to the ratio of Si becoming excessive. On the other hand, if "x" becomes larger than an upper limit value, energy density is decreased due to the Si ratio being too small. The range of "x" is more preferably $0.5 \leq x \leq 1.5$, and further preferably $0.7 \leq x \leq 1.2$.

In $SiO_x$ described above, an alloying reaction between lithium and silicon in the Si phase is considered to occur during charging and discharging of the lithium ion secondary battery. This alloying reaction is considered to contribute to charging and discharging of the lithium ion secondary battery. Also in the negative electrode active material including tin described later, charging and discharging are considered to occur by an alloying reaction between tin and lithium.

Specific examples of the negative electrode active material include materials containing tin. More specific examples include Sn elemental substance, tin alloys such as Cu—Sn and Co—Sn, amorphous tin oxides, and tin silicon oxides. Examples of the amorphous tin oxides include $SnB_{0.4}P_{0.6}O_{3.1}$, and examples of the tin silicon oxides include $SnSiO_3$.

The material containing silicon and the material containing tin described above are each preferably made into a composite with a carbon material to be used as the negative electrode active material. By using those materials as a composite, the structure particularly of silicon and/or tin is stabilized, and durability of the negative electrode is improved. Making a composite mentioned above may be performed by a known method. As the carbon material used in the composite, a graphite, a hard carbon, a soft carbon, etc. may be used. The graphite may be a natural graphite or an artificial graphite.

Specific examples of the negative electrode active material include lithium titanate having a spinel structure such as $Li_{4+x}Ti_{5+y}O_{12}$ ($-1 \leq x \leq 4$, $-1 \leq y \leq 1$) and lithium titanate having a ramsdellite structure such as $Li_2Ti_3O_7$.

Specific examples of the negative electrode active material include graphites having a value of long axis/short axis of 1 to 5, and preferably 1 to 3. Here, the long axis means the length of the longest portion of a graphite particle. The short axis means the longest length in directions perpendicular to the long axis. Spheroidal graphites and meso carbon micro beads correspond to the graphite. The spheroidal graphites mean carbon materials which are artificial graphite, natural graphite, easily graphitizable carbon, and hardly graphitizable carbon, for example, and which have spheroidal or substantially spheroidal shapes.

Spheroidal graphite is obtained by grinding graphite into flakes by means of an impact grinder having a relatively small crushing force and by compressing and spheroidizing the flakes. Examples of the impact grinder include a hammer mill and a pin mill. The above operation is preferably performed with the outer-circumference line speed of the hammer or the pin of the mill set at about 50 to 200 m/s. Supply and ejection of graphite with respect to such mills are preferably performed in association with a current of air or the like.

The graphite preferably has a BET specific surface area in a range of 0.5 to 15 $m^2/g$. When the BET specific surface area is too large, side reaction between the graphite and the electrolytic solution is accelerated in some cases. When the BET specific surface area is too small, reaction resistance of the graphite becomes large in some cases.

The negative electrode includes a current collector, and a negative electrode active material layer bound to the surface of the current collector.

The current collector refers to a high-conductivity electron conductor that is chemically inert for continuously sending a flow of current to the electrode during discharging or charging of the lithium ion secondary battery. Examples of the current collector include at least one selected from silver, copper, gold, aluminum, tungsten, cobalt, zinc, nickel, iron, platinum, tin, indium, titanium, ruthenium, tantalum, chromium, or molybdenum, and metal materials such as stainless steel. The current collector may be coated with a known protective layer. One obtained by treating the surface of the current collector with a known method may be used as the current collector.

The current collector takes forms such as a foil, a sheet, a film, a line shape, a bar shape, and a mesh. Thus, as the current collector, for example, metal foils such as copper foil, nickel foil, aluminum foil, and stainless steel foil are suitably used. When the current collector is in the form of a foil, a sheet, or a film, the thickness thereof is preferably in a range of 1 μm to 100 μm.

The negative electrode active material layer includes a negative electrode active material, and, if necessary, a binding agent and/or a conductive additive.

The binding agent serves to adhere the active material and the conductive additive to the surface of the current collector.

As the binding agent, a known binding agent may be used such as a fluorine-containing resin such as polyvinylidene fluoride, polytetrafluoroethylene, or fluororubber, a thermoplastic resin such as polypropylene or polyethylene, an imide-based resin such as polyimide or polyamide-imide, an alkoxysilyl group-containing resin, or a styrene butadiene rubber.

In addition, a polymer having a hydrophilic group may be used as the binding agent. Examples of the hydrophilic group of the polymer having a hydrophilic group include carboxyl group, sulfo group, silanol group, amino group, hydroxyl group, and phosphoric acid-based group such as phosphoric acid group. Among those described above, a polymer containing a carboxyl group in the molecule thereof, such as polyacrylic acid, carboxymethyl cellulose, and polymethacrylic acid, or a polymer containing a sulfo group such as poly(p-styrenesulfonic acid) is preferable.

A polymer containing a large number of carboxyl groups and/or sulfo groups, such as polyacrylic acid or a copolymer of acrylic acid and vinylsulfonic acid, is water soluble. The polymer containing the hydrophilic group is preferably a water soluble polymer, and is preferably a polymer containing multiple carboxyl groups and/or sulfo groups in a single molecule thereof in terms of the chemical structure.

A polymer containing a carboxyl group in the molecule thereof is produced through, for example, a method of polymerizing an acid monomer or a method of imparting a carboxyl group to a polymer. Examples of the acid monomer include acid monomers having one carboxyl group in respective molecules such as acrylic acid, methacrylic acid, vinylbenzoic acid, crotonic acid, pentenoic acid, angelic acid, and tiglic acid, and acid monomers having two or more carboxyl groups in respective molecules such as itaconic acid, mesaconic acid, citraconic acid, fumaric acid, maleic acid, 2-pentenedioic acid, methylenesuccinic acid, allylmalonic acid, isopropylidene succinic acid, 2,4-hexadienedioic acid, and acetylene dicarboxylic acid.

A copolymer obtained through polymerization of two or more types of acid monomers selected from the acid monomers described above may be used as the binding agent.

For example, as disclosed in JP2013065493(A), a polymer that includes in the molecule thereof an acid anhydride group formed through condensation of carboxyl groups of a copolymer of acrylic acid and itaconic acid is also preferably used as the binding agent. Since the binding agent has a structure derived from a monomer with high acidity by having two or more carboxyl groups in a single molecule thereof, the binding agent is considered to easily trap the lithium ions and the like before a degradation reaction of the electrolytic solution occurs during charging. Furthermore, although the polymer has an increased acidity because the polymer has more carboxyl groups per monomer when compared to polyacrylic acid and polymethacrylic acid, the acidity is not increased too much because a certain amount of carboxyl groups have changed into acid anhydride groups. Therefore, the secondary battery having the negative electrode using the polymer as the binding agent has improved initial efficiency and improved input-output characteristics.

The blending ratio of the binding agent in the negative electrode active material layer in mass ratio is preferably negative electrode active material:binding agent=1:0.005 to 1:0.3. The reason is that when too little of the binding agent is contained, moldability of the electrode deteriorates, whereas too much of the binding agent is contained, energy density of the electrode becomes low.

The conductive additive is added for increasing conductivity of the electrode. Thus, the conductive additive is preferably added optionally when conductivity of the electrode is insufficient, and does not have to be added when conductivity of the electrode is sufficiently good. As the conductive additive, a high-conductivity electron conductor that is chemically inert may be used, and examples thereof include carbonaceous fine particles such as carbon black, graphite, acetylene black, Ketchen black (registered trademark), vapor grown carbon fiber (VGCF), and various metal particles. With regard to the conductive additive described above, a single type by itself, or a combination of two or more types may be added to the active material layer. The blending ratio of the conductive additive in the negative electrode active material layer in mass ratio is preferably negative electrode active material:conductive additive=1: 0.01 to 1:0.5. The reason is that when too little of the conductive additive is contained, efficient conducting paths are not formed, whereas when too much of the conductive additive is contained, moldability of the negative electrode active material layer deteriorates and energy density of the electrode becomes low.

The positive electrode used in the lithium ion secondary battery includes a positive electrode active material capable of occluding and releasing lithium ions. The positive electrode includes a current collector and a positive electrode active material layer bound to the surface of the current collector. The positive electrode active material layer includes a positive electrode active material, and, if necessary, a binding agent and/or a conductive additive. The current collector of the positive electrode is not limited in particular as long as the current collector is a metal capable of withstanding a voltage suited for the active material that is used. Examples of the current collector include at least one selected from silver, copper, gold, aluminum, tungsten, cobalt, zinc, nickel, iron, platinum, tin, indium, titanium, ruthenium, tantalum, chromium, and molybdenum, and metal materials such as stainless steel.

When the potential of the positive electrode is set to not lower than 4V using lithium as reference, aluminum is preferably used as the current collector.

Specifically, as the positive electrode current collector, one formed from aluminum or an aluminum alloy is preferably used. Here, aluminum refers to pure aluminum, and an aluminum whose purity is not less than 99.0% is referred to as pure aluminum. An alloy obtained by adding various elements to pure aluminum is referred to as an aluminum alloy. Examples of the aluminum alloy include those that are Al—Cu based, Al—Mn based, Al—Fe based, Al—Si based, Al—Mg based, Al—Mg—Si based, and Al—Zn—Mg based.

In addition, specific examples of aluminum or the aluminum alloy include A1000 series alloys (pure aluminum based) such as JIS A1085, A1N30, etc., A3000 series alloys (Al—Mn based) such as JIS A3003, A3004, etc., and A8000 series alloys (Al—Fe based) such as JIS A8079, A8021, etc.

The current collector may be coated with a known protective layer. One obtained by treating the surface of the current collector with a known method may be used as the current collector.

The current collector takes forms such as a foil, a sheet, a film, a line shape, a bar shape, and a mesh. Thus, as the current collector, for example, metal foils such as copper foil, nickel foil, aluminum foil, and stainless steel foil are suitably used. When the current collector is in the form of a foil, a sheet, or a film, the thickness thereof is preferably in a range of 1 μm to 100 μm.

As the binding agent and the conductive additive for the positive electrode, those described with respect to the negative electrode are used at similar blending ratios.

Examples of the positive electrode active material include layered compounds that are $Li_aNi_bCo_cMn_dD_eO_f$ ($0.2 \le a \le 1.2$; $b+c+d+e=1$; $0 \le e<1$; D is at least one element selected from Li, Fe, Cr, Cu, Zn, Ca, Mg, S, Si, Na, K, Al, Zr, Ti, P, Ga, Ge, V, Mo, Nb, W, or La; and $1.7 \le f \le 2.1$) and $Li_2MnO_3$. Additional examples of the positive electrode active material include metal oxides having a spinel structure such as $LiMn_2O_4$, a solid solution formed from a mixture of a metal oxide having a spinel structure and a layered compound, and polyanion-based compounds represented by $LiMPO_4$, $LiMVO_4$, $Li_2MSiO_4$ (where "M" is selected from at least one of Co, Ni, Mn, or Fe), or the like. Further additional examples of the positive electrode active material include tavorite-based compounds represented by $LiMPO_4F$ ("M" is a transition metal) such as $LiFePO_4F$ and borate-based compounds represented by $LiMBO_3$ ("M" is a transition metal) such as $LiFeBO_3$. Any metal oxide used as the positive electrode active material may have a basic composition of the composition formulae described above, and those in which a metal element included in the basic composition is substituted with another metal element may also be used. In addition, as the positive electrode active material, one that does not contain a charge carrier (e.g., a lithium ion contributing to the charging and discharging) may also be used. For example, elemental substance sulfur, a compound that is a composite of sulfur and carbon, metal sulfides such as $TiS_2$, oxides such as $V_2O_5$ and $MnO_2$, polyaniline and anthraquinone and compounds containing such aromatics in the chemical structure, conjugate-based materials such as conjugate diacetic acid-based organic matters, and known other materials may be used. Furthermore, a compound having a stable radical such as nitroxide, nitronyl nitroxide, galvinoxyl, and phenoxyl may be used as the positive electrode active material. When a positive electrode active material not containing a charge carrier such as lithium is to be used, a charge carrier has to be added in advance to the positive electrode and/or the negative electrode using a known method. The charge carrier may be added in an ionic state, or may be added in a nonionic state such as a metal. For example, when the charge carrier is lithium, a lithium foil may be pasted to and integrated with the positive electrode and/or the negative electrode.

Specific examples of the positive electrode active material include $Li_xA_yMn_{2-y}O_4$ having a spinel structure ("A" is at least one element selected from Ca, Mg, S, Si, Na, K, Al, P, Ga, or Ge, and/or at least one type of metal element selected from transition metal elements, $0<x \le 2.2$, $0 \le y \le 1$). More specific examples include $LiMn_2O_4$, and $LiNi_{0.5}Mn_{1.5}O_4$.

Examples of the specific positive electrode active material include a compound represented by $Li_aNi_bCo_cMn_dD_eO_f$ having a layered rock salt structure ($0.2 \le a \le 1.2$, $b+c+d+e=1$, D is at least one element selected from Li, Fe, Cr, Cu, Zn, Ca, Mg, S, Si, Na, K, Al, Zr, Ti, P, Ga, Ge, V, Mo, Nb, W, and La, and $1.7 \le f \le 2.1$). Here, examples of a suitable range for "a" include $0.7 \le a \le 1.2$ and examples of a suitable range for "b" include and $0.2 \le b \le 0.55$, examples of a suitable range for "c" include $0.1 \le c \le 0.8$ and $0.2 \le c \le 0.55$, example of a suitable range for "d" include $0.01 \le d \le 0.5$ and $0.1 \le d \le 0.4$, examples of a suitable range for "e" include $0 \le e \le 0.3$ and $0 \le e \le 0.1$, and examples of a suitable range for "f" include $1.8 \le c \le 2.05$.

More specific examples of the compound having a layered rock salt structure include $LiNi_{0.5}Co_{0.3}Mn_{0.2}O_2$, $LiNi_{0.5}Co_{0.2}Mn_{0.3}O_2$, $LiNi_{1/3}Co_{1/3}Mn_{1/3}O_2$, $LiNi_{0.5}Mn_{0.5}O_2$, $LiNi_{0.75}Co_{0.1}Mn_{0.15}O_2$, $LiMnO_2$, and $LiCoO_2$. Another specific example of the positive electrode active material includes $Li_2MnO_3$—$LiCoO_2$.

Specific examples of the positive electrode active material include LiFePO$_4$, Li$_2$FeSiO$_4$, LiCoPO$_4$, Li$_2$CoPO$_4$, Li$_2$MnPO$_4$, Li$_2$MnSiO$_4$, and Li$_2$CoPO$_4$F.

These positive electrode active materials may be those having a reaction potential not lower than 4.5 V when a Li$^+$/Li electrode is used as reference. Here, "reaction potential" refers to a potential that causes oxidation-reduction reaction of the positive electrode active material through charging and discharging. The reaction potential is based on a Li$^+$/Li electrode. Although the reaction potential varies within some range in some cases, "reaction potential" in the present specification refers to the average value of the reaction potentials in the range, and when multiple levels of the reaction potential exist, refers to the average value of the multiple levels of the reaction potentials. Examples of the positive electrode active material having a reaction potential not lower than 4.5 V when a Li$^+$/Li electrode is used as reference include: Li$_x$A$_y$Mn$_{2-y}$O$_4$ (A is at least one element selected from Ca, Mg, S, Si, Na, K, Al, P, Ga, and Ge and/or at least one type of metal element selected from transition metal elements, $0<x\leq 2.2$, $0\leq y\leq 1$) which is a metal oxide having a spinel structure such as LiNi$_{0.5}$Mn$_{1.5}$O$_4$; LiCoPO$_4$; Li$_2$CoPO$_4$F; Li$_2$MnO$_3$—LiMO$_2$ (M is selected from at least one of Co, Ni, Mn, and Fe); Li$_2$MnSiO$_4$; and the like.

In order to form the active material layer on the surface of the current collector, the active material may be applied on the surface of the current collector using a known conventional method such as roll coating method, die coating method, dip coating method, doctor blade method, spray coating method, and curtain coating method. Specifically, an active material layer forming composition containing the active material and, if necessary, the binding agent and the conductive additive, is prepared, and, after adding a suitable solvent to this composition to obtain a paste, the paste is applied on the surface of the current collector and then dried. Examples of the solvent include N-methyl-2-pyrrolidone, methanol, methyl isobutyl ketone, and water. In order to increase electrode density, compression may be performed after drying.

A separator is used in the lithium ion secondary battery, if necessary. The separator is for separating the positive electrode and the negative electrode to allow passage of lithium ions while preventing short circuit due to a contact of both electrodes. As the separator, one that is known may be used. Examples of the separator include porous materials, nonwoven fabrics, and woven fabrics using one or more types of materials having electrical insulation property such as: synthetic resins such as polytetrafluoroethylene, polypropylene, polyethylene, polyimide, polyamide, polyaramide (aromatic polyamide), polyester, and polyacrylonitrile; polysaccharides such as cellulose and amylose; natural polymers such as fibroin, keratin, lignin, and suberin; and ceramics. In addition, the separator may have a multilayer structure.

A specific method for producing the lithium ion secondary battery of the present invention is described.

An electrode assembly is formed from the positive electrode, the negative electrode, and, if necessary, the separator interposed therebetween. The electrode assembly may be a laminated type obtained by stacking the positive electrode, the separator, and the negative electrode, or a wound type obtained by winding the positive electrode, the separator, and the negative electrode. The lithium ion secondary battery is preferably formed by respectively connecting, using current collecting leads or the like, the positive electrode current collector to a positive electrode external connection terminal and the negative electrode current collector to a negative electrode external connection terminal, and then adding the electrolytic solution of the present invention to the electrode assembly. In addition, the lithium ion secondary battery of the present invention preferably executes charging and discharging in a voltage range suitable for the types of active materials contained in the electrodes.

The form of the lithium ion secondary battery of the present invention is not limited in particular, and various forms such as a cylindrical type, a square type, a coin type, a laminated type, etc., are used.

The lithium ion secondary battery of the present invention may be mounted on a vehicle. The vehicle may be a vehicle that uses, as all or a part of the source of power, electrical energy obtained from the lithium ion secondary battery, and examples thereof include electric vehicles and hybrid vehicles. When the lithium ion secondary battery is to be mounted on the vehicle, a plurality of the lithium ion secondary batteries may be connected in series to form an assembled battery. Other than the vehicles, examples of instruments on which the lithium ion secondary battery may be mounted include various home appliances, office instruments, and industrial instruments driven by a battery such as personal computers and portable communication devices. In addition, the lithium ion secondary battery of the present invent ion may be used as power storage devices and power smoothing devices for wind power generation, photovoltaic power generation, hydroelectric power generation, and other power systems, power supply sources for auxiliary machineries and/or power of ships, etc., power supply sources for auxiliary machineries and/or power of aircraft and spacecraft, etc., auxiliary power supply for vehicles that do not use electricity as a source of power, power supply for movable household robots, power supply for system backup, power supply for uninterruptible power supply devices, and power storage devices for temporarily storing power required for charging at charge stations for electric vehicles.

A capacitor of the present invention may be formed by replacing, with active carbon or the like that is used as a polarized electrode material, a part or all of the negative electrode active material or the positive electrode active material, or a part or all of the negative electrode active material and the positive electrode active material, in the lithium ion secondary battery of the present invention described above. Examples of the capacitor of the present invention include electrical double layer capacitors and hybrid capacitors such as lithium ion capacitors. As the description of the capacitor of the present invention, the description of the lithium ion secondary battery of the present invention above in which "lithium ion secondary battery" is replaced by "capacitor" as appropriate is used.

Although embodiments of the electrolytic solution of the present invention have been described above, the present invention is not limited to the embodiments. Without departing from the gist of the present invention, the present invention can be implemented in various modes with modifications and improvements, etc., that can be made by a person skilled in the art.

EXAMPLES

In the following, the present invention is specifically described by presenting Examples and Comparative Examples. The present invention is not limited to these Examples.

Example 1-1

About 5 mL of DMC serving as the linear carbonate represented by general formula (1-1) was placed in a flask provided with a stirring bar. Under a stirring condition, to the DMC in the flask, $LiPF_6$ serving as the metal salt was gradually added to be dissolved. $LiPF_6$ was added so that the total amount of $LiPF_6$ became 10.01 g, and further, DMC was added so that the total amount of DMC became 11.50 g, and the resultant mixture was stirred. Since a small amount of undissolved $LiPF_6$ was visually observed, DMC was added so that the total amount of DMC became 11.87 g, thereby dissolving $LiPF_6$. This solution was used as the electrolytic solution of Example 1-1. The above production was performed within a glovebox under an inert gas atmosphere.

The concentration of $LiPF_6$ in the electrolytic solution of Example 1-1 was 4.4 mol/L. In the electrolytic solution of Example 1-1, 2 mol of DMC is contained relative to 1 mol of $LiPF_6$.

Example 1-2

About 5 mL of DMC serving as the linear carbonate represented by general formula (1-1) was placed in a flask provided with a stirring bar. Under a stirring condition, to the DMC in the flask, $LiPF_6$ serving as the metal salt was gradually added to be dissolved. $LiPF_6$ was added so that the total amount of $LiPF_6$ became 8.02 g, and further DMC was added so that the total amount of DMC became 11.89 g, thereby dissolving $LiPF_6$. This solution was used as the electrolytic solution of Example 1-2. The above production was performed within a glovebox under an inert gas atmosphere.

The concentration of $LiPF_6$ in the electrolytic solution of Example 1-2 was 3.75 mol/L. In the electrolytic solution of Example 1-2, 2.5 mol of DMC is contained relative to 1 mol of $LiPF_6$.

Example 1-3

An electrolytic solution of Example 1-3 was produced by a method similar to that in Example 1-2, except for using a total amount of 6.99 g of $LiPF_6$ and a total amount of 12.43 g of DMC. The concentration of $LiPF_6$ in the electrolytic solution of Example 1-3 was 3.19 mol/L. In the electrolytic solution of Example 1-3, 3 mol of DMC is contained relative to 1 mol of $LiPF_6$.

Example 1-4

8.02 mL of the electrolytic solution of Example 1-2 was transferred to a 10-mL measuring flask, DMC was added thereto so that a volume of 10 mL of the solution was obtained. This solution was used as the electrolytic solution of Example 1-4. The above production was performed within a glovebox under an inert gas atmosphere. The concentration of $LiPF_6$ in the electrolytic solution of Example 1-4 was 3 mol/L. In the electrolytic solution of Example 1-4, 3.31 mol of DMC is contained relative to 1 mol of $LiPF_6$.

Example 1-5

An electrolytic solution of Example 1-5 was produced by a method similar to that in Example 1-4, except for using 6.67 mL of the electrolytic solution of Example 1-4. The concentration of $LiPF_6$ in the electrolytic solution of Example 1-5 was 2 mol/L. In the electrolytic solution of Example 1-5, 5.31 mol of DMC is contained relative to 1 mol of $LiPF_6$.

Example 1-6

An electrolytic solution of Example 1-6 was produced by a method similar to that in Example 1-5, except that vinylene carbonate was added so that 0.2 mass % of vinylene carbonate in the entire electrolytic solution was attained. The concentration of $LiPF_6$ in the electrolytic solution of Example 1-6 was 2 mol/L. In the electrolytic solution of Example 1-6, 5.31 mol of DMC is contained relative to 1 mol of $LiPF_6$.

Example 2-1

About 5 mL of EMC serving as the linear carbonate represented by general formula (1-1) was placed in a flask provided with a stirring bar. Under a stirring condition, to the EMC in the flask, $LiPF_6$ serving as the metal salt was gradually added to be dissolved. $LiPF_6$ was added so that the total amount of $LiPF_6$ became 8.01 g, further, EMC was added so that the total amount of EMC became 10.98 g, and the resultant mixture was stirred. Since a small amount of undissolved $LiPF_6$ was visually observed, EMC was added so that the total amount of EMC became 11.78 g, thereby dissolving $LiPF_6$. This solution was used as the electrolytic solution of Example 2-1. The above production was performed within a glovebox under an inert gas atmosphere.

The concentration of $LiPF_6$ in the electrolytic solution of Example 2-1 was 3.58 mol/L. In the electrolytic solution of Example 2-1, 2.15 mol of EMC is contained relative to 1 mol of $LiPF_6$.

Example 3-1

About 5 mL of DEC serving as the linear carbonate represented by general formula (1-1) was placed in a flask provided with a stirring bar. Under a stirring condition, to the DEC in the flask, $LiPF_6$ serving as the metal salt was gradually added to be dissolved. $LiPF_6$ was added so that the total amount of $LiPF_6$ became 8.01 g, further, DEC was added so that the total amount of EMC became 12.46 g, and the resultant mixture was stirred. Since a small amount of undissolved $LiPF_6$ was visually observed, DEC was added so that the total amount of DEC became 16.72 g, thereby dissolving $LiPF_6$. This solution was used as the electrolytic solution of Example 3-1. The above production was performed within a glovebox under an inert gas atmosphere.

The concentration of $LiPF_6$ in the electrolytic solution of Example 3-1 was 2.62 mol/L. In the electrolytic solution of Example 3-1, 2.69 mol of DEC is contained relative to 1 mol of $LiPF_6$.

Example 4-1

About 5 mL of DMC serving as the linear carbonate represented by general formula (1-1) was placed in a flask provided with a stirring bar. Under a stirring condition, to the DMC in the flask, $LiBF_4$ serving as the metal salt was gradually added to be dissolved. $LiBF_4$ was added so that the total amount of $LiBF_4$ became 10 g, further, DMC was added so that the total amount of DMC became 9.61 g, and the resultant mixture was stirred. Since a small amount of undissolved $LiBF_4$ was visually observed, DMC was added so that the total amount of DMC became 12.74 g, thereby dissolving $LiBF_4$. This solution was used as the electrolytic solution of Example 4-1. The above production was performed within a glovebox under an inert gas atmosphere.

The concentration of $LiBF_4$ in the electrolytic solution of Example 4-1 was 6.46 mol/L. In the electrolytic solution of Example 4-1, 1.33 mol of DMC is contained relative to 1 mol of $LiBF_4$.

Example 4-2

About 5 mL of DMC serving as the linear carbonate represented by general formula (1-1) was placed in a flask provided with a stirring bar. Under a stirring condition, to the DMC in the flask, $LiBF_4$ serving as the metal salt was gradually added to be dissolved. $LiBF_4$ was added so that the total amount of $LiBF_4$ became 10 g, and further, DMC was added so that the total amount of DMC became 19.22 g, thereby dissolving $LiBF_4$. This solution was used as the electrolytic solution of Example 4-2. The above production was performed within a glovebox under an inert gas atmosphere.

The concentration of $LiBF_4$ in the electrolytic solution of Example 4-2 was 4.92 mol/L. In the electrolytic solution of Example 4-2, 2 mol of DMC is contained relative to 1 mol of $LiBF_4$.

Example 4-3

An electrolytic solution of Example 4-3 was produced by a method similar to that in Example 4-2, except for using a total amount of 5.01 g of $LiBF_4$ and a total amount of 12.03 g of DMC. The concentration of $LiBF_4$ in the electrolytic solution of Example 4-3 was 3.99 mol/L. In the electrolytic solution of Example 4-3, 2.5 mol of DMC is contained relative to 1 mol of $LiBF_4$.

Example 4-4

An electrolytic solution of Example 4-4 was produced by a method similar to that in Example 4-2, except for using a total amount of 5 g of $LiBF_4$ and a total amount of 14.41 g of DMC. The concentration of $LiBF_4$ in the electrolytic solution of Example 4-4 was 3.42 mol/L. In the electrolytic solution of Example 4-4, 3 mol of DMC is contained relative to 1 mol of $LiBF_4$.

Example 4-5

6.10 mL of the electrolytic solution of Example 4-2 was transferred to a 10-mL measuring flask, DMC was added thereto so that a volume of 10 mL of the solution was obtained. This solution was used as the electrolytic solution of Example 4-5. The above production was performed within a glovebox under an inert gas atmosphere. The concentration of $LiBF_4$ in the electrolytic solution of Example 4-5 was 3 mol/L. In the electrolytic solution of Example 4-5, 3.48 mol of DMC is contained relative to 1 mol of $LiBF_4$.

Example 4-6

An electrolytic solution of Example 4-6 was produced by a method similar to that in Example 4-5, except for using 4.07 mL of the electrolytic solution of Example 4-2. The concentration of $LiBF_4$ in the electrolytic solution of Example 4-6 was 2 mol/L. In the electrolytic solution of Example 4-6, 5.46 mol of DMC is contained relative to 1 mol of $LiBF_4$.

Example 5-1

About 5 mL of EMC serving as the linear carbonate represented by general formula (1-1) was placed in a flask provided with a stirring bar. Under a stirring condition, to the EMC in the flask, $LiBF_4$ serving as the metal salt was gradually added to be dissolved. $LiBF_4$ was added so that the total amount of $LiBF_4$ became 6.01 g, and further, EMC was added so that the total amount of EMC became 13.35 g, thereby dissolving $LiBF_4$. This solution was used as the electrolytic solution of Example 5-1. The above production was performed within a glovebox under an inert gas atmosphere.

The concentration of $LiBF_4$ in the electrolytic solution of Example 5-1 was 4.04 mol/L. In the electrolytic solution of Example 5-1, 2 mol of EMC is contained relative to 1 mol of $LiBF_4$.

Example 6-1

About 5 mL of DEC serving as the linear carbonate represented by general formula (1-1) was placed in a flask provided with a stirring bar. Under a stirring condition, to the DEC in the flask, $LiBF_4$ serving as the metal salt was gradually added to be dissolved. $LiBF_4$ was added so that the total amount of $LiBF_4$ became 6 g, further, DEC was added so that the total amount of DEC became 15.12 g, and the resultant mixture was stirred. Since a small amount of undissolved $LiBF_4$ was visually observed, DEC was added so that the total amount of DEC became 16.84 g, thereby dissolving $LiBF_4$. This solution was used as the electrolytic solution of Example 6-1. The above production was performed within a glovebox under an inert gas atmosphere.

The concentration of $LiBF_4$ in the electrolytic solution of Example 6-1 was 3.19 mol/L. In the electrolytic solution of Example 6-1, 2.23 mol of DEC is contained relative to 1 mol of $LiBF_4$.

Comparative Example 1-1

About 5 mL of acetonitrile was placed in a flask provided with a stirring bar. Under a stirring condition, to the acetonitrile in the flask, $LiPF_6$ serving as the metal salt was gradually added. $LiPF_6$ was added so that the total amount of $LiPF_6$ became 10.01 g, further, acetonitrile was added so that the total amount of acetonitrile became 5.41 g, and the resultant mixture was stirred. Since undissolved $LiPF_6$ was visually observed, the solution was heated to 80° C. and stirred. However, undissolved $LiPF_6$ was still visually observed. 10.01 g of $LiPF_6$ failed to be dissolved in 5.41 g of acetonitrile. If 10.01 g of $LiPF_6$ had been dissolved in 5.41 g of acetonitrile, 2 mol of acetonitrile should have been contained in the resultant solution, relative to 1 mol of $LiPF_6$.

Comparative Example 1-2

About 5 mL of 1, 2-dimethoxyethane was placed in a flask provided with a stirring bar. Under a stirring condition, to the 1,2-dimethoxyethane in the flask, $LiPF_6$ serving as the metal salt was gradually added. $LiPF_6$ was added so that the total amount of $LiPF_6$ became 5 g, further, 1,2-dimethoxyethane was added so that the total amount of 1,2-dimethoxyethane became 5.93 g, and the resultant mixture was stirred. Since undissolved $LiPF_6$ was visually observed, the solution was heated to 80° C. and stirred. However, undissolved $LiPF_6$ was still visually observed. 5 g of $LiPF_6$ failed to be dissolved in 5.93 g of 1,2-dimethoxyethane. If 5 g of $LiPF_6$ had been dissolved in 5.93 g of 1,2-dimethoxyethane, 2 mol of 1,2-dimethoxyethane should have been contained in the resultant solution, relative to 1 mol of $LiPF_6$.

Comparative Example 1-3

About 5 mL of N,N-dimethylformamide was placed in a flask provided with a stirring bar. Under a stirring condition, to the N,N-dimethylformamide in the flask, $LiPF_6$ serving as the metal salt was gradually added. $LiPF_6$ was added so that the total amount of $LiPF_6$ became 7 g, further, N,N-dimethylformamide was added so that the total amount of N,N-dimethylformamide became 6.74 g, and the resultant mixture was stirred. Since undissolved $LiPF_6$ was visually observed, the solution was heated to 80° C. and stirred. However, undissolved $LiPF_6$ was still visually observed. 7 g of $LiPF_6$ failed to be dissolved in 6.74 g of N,N-dimethylformamide. If 7 g of $LiPF_6$ had been dissolved in 6.74 g of N,N-dimethylformamide, 2 mol of N,N-dimethylformamide should have been contained in the resultant solution, relative to 1 mol of $LiPF_6$.

Comparative Example 2-1

An electrolytic solution of Comparative Example 2-1 was produced by a method similar to that in Example 1-4, except for using 3.13 mL of the electrolytic solution of Example 1-3. The concentration of $LiPF_6$ in the electrolytic solution of Comparative Example 2-1 was 1 mol/L. In the electrolytic solution of Comparative Example 2-1, 11.24 mol of DMC is contained relative to 1 mol of $LiPF_6$.

Comparative Example 3-1

An electrolytic solution of Comparative Example 3-1 was produced by a method similar to that in Example 4-5, except for using 2.92 mL of the electrolytic solution of Example 4-4. The concentration of $LiBF_4$ in the electrolytic solution of Comparative Example 3-1 was 1 mol/L. In the electrolytic solution of Comparative Example 3-1, 11.37 mol of DMC is contained relative to 1 mol of $LiBF_4$.

Comparative Example 4-1

$LiPF_6$ was dissolved in a mixed solvent obtained by mixing ethylene carbonate (hereinafter, sometimes referred to as "EC"), ethyl methyl carbonate, and dimethyl carbonate (at a volume ratio of 3:3:4; hereinafter, this mixed solvent is sometimes referred to as "EC/EMC/DMC"), whereby an electrolytic solution of Comparative Example 4-1 having $LiPF_6$ at a concentration of 1.0 mol/L was produced. The above production was performed within a glovebox under an inert gas atmosphere. In the electrolytic solution of Comparative Example 4-1, about 10 mol of EC/EMC/DMC is contained relative to 1 mol of $LiPF_6$.

Table 1-1 shows a list of the electrolytic solutions of Examples. Table 1-2 shows a list of the electrolytic solutions of Comparative Examples.

TABLE 1-1

| | Metal salt | Organic solvent | Number of moles of organic solvent/ number of moles of metal salt | Concentration of metal salt (mol/L) |
|---|---|---|---|---|
| Example 1-1 | $LiPF_6$ | DMC | 2 | 4.4 |
| Example 1-2 | $LiPF_6$ | DMC | 2.5 | 3.75 |
| Example 1-3 | $LiPF_6$ | DMC | 3 | 3.19 |

TABLE 1-1-continued

| | Metal salt | Organic solvent | Number of moles of organic solvent/ number of moles of metal salt | Concentration of metal salt (mol/L) |
|---|---|---|---|---|
| Example 1-4 | $LiPF_6$ | DMC | 3.31 | 3 |
| Example 1-5 | $LiPF_6$ | DMC | 5.31 | 2 |
| Example 1-6*) | $LiPF_6$ | DMC | 5.31 | 2 |
| Example 2-1 | $LiPF_6$ | EMC | 2.15 | 3.58 |
| Example 3-1 | $LiPF_6$ | DEC | 2.69 | 2.62 |
| Example 4-1 | $LiBF_4$ | DMC | 1.33 | 6.46 |
| Example 4-2 | $LiBF_4$ | DMC | 2 | 4.92 |
| Example 4-3 | $LiBF_4$ | DMC | 2.5 | 3.99 |
| Example 4-4 | $LiBF_4$ | DMC | 3 | 3.42 |
| Example 4-5 | $LiBF_4$ | DMC | 3.48 | 3 |
| Example 4-6 | $LiBF_4$ | DMC | 5.46 | 2 |
| Example 5-1 | $LiBF_4$ | EMC | 2 | 4.04 |
| Example 6-1 | $LiBF_4$ | DEC | 2.23 | 3.19 |

*)Example 1-6 contains vinylene carbonate.

TABLE 1-2

| | Metal salt | Organic solvent | Number of moles of organic solvent/number of moles of metal salt | Concentration of metal salt (mol/L) |
|---|---|---|---|---|
| Comparative Example 1-1 | $LiPF_6$ | AN | Solution having mole ratio of 2 not obtained | |
| Comparative Example 1-2 | $LiPF_6$ | DME | Solution having mole ratio of 2 not obtained | |
| Comparative Example 1-3 | $LiPF_6$ | DMF | Solution having mole ratio of 2 not obtained | |
| Comparative Example 2-1 | $LiPF_6$ | DMC | 11.24 | 1 |
| Comparative Example 3-1 | $LiBF_4$ | DMC | 11.37 | 1 |
| Comparative Example 4-1 | $LiPF_6$ | EC/EMC/DMC | 10 | 1 |

The results of Example 1-1 and Comparative Examples 1-1 to 1-3 suggest a specific metal salt dissolving ability of the specific organic solvent.

Evaluation Example 1: Ionic Conductivity

Ionic conductivities of the electrolytic solutions of Examples and Comparative Examples were measured under the following condition. Table 2-1 and Table 2-2 show the results.

Ionic Conductivity Measuring Condition

Under an Ar atmosphere, an electrolytic solution was sealed in a glass cell that had a platinum electrode and whose cell constant was known, and impedance thereof was measured at 25° C., 10 kHz. Ionic conductivity was calculated from the measurement result of the impedance. As a measurement instrument, Solartron 147055BEC (Solartron Analytical) was used.

TABLE 2-1

| | Metal salt | Organic solvent | Number of moles of organic solvent/number of moles of metal salt | Ionic conductivity (mS/cm) |
|---|---|---|---|---|
| Example 1-1 | $LiPF_6$ | DMC | 2 | 1.89 |
| Example 1-2 | $LiPF_6$ | DMC | 2.5 | 3.08 |
| Example 1-3 | $LiPF_6$ | DMC | 3 | 4.54 |
| Example 1-4 | $LiPF_6$ | DMC | 3.31 | 5.72 |
| Example 1-5 | $LiPF_6$ | DMC | 5.31 | 9.42 |
| Example 2-1 | $LiPF_6$ | EMC | 2.15 | 1.45 |
| Example 3-1 | $LiPF_6$ | DEC | 2.69 | 2.18 |
| Example 4-1 | $LiBF_4$ | DMC | 1.33 | 0.52 |
| Example 4-2 | $LiBF_4$ | DMC | 2 | 1.40 |
| Example 4-3 | $LiBF_4$ | DMC | 2.5 | 1.79 |
| Example 4-4 | $LiBF_4$ | DMC | 3 | 2.06 |
| Example 4-5 | $LiBF_4$ | DMC | 3.48 | 2.11 |
| Example 4-6 | $LiBF_4$ | DMC | 5.46 | 1.58 |
| Example 5-1 | $LiBF_4$ | EMC | 2 | 0.81 |
| Example 6-1 | LiBF4 | DEC | 2.23 | 0.44 |

TABLE 2-2

| | Metal salt | Organic solvent | Number of moles of organic solvent/number of moles of metal salt | Ionic conductivity (mS/cm) |
|---|---|---|---|---|
| Comparative Example 2-1 | $LiPF_6$ | DMC | 11.24 | 6.44 |
| Comparative Example 3-1 | $LiBF_4$ | DMC | 11.37 | 0.46 |
| Comparative Example 4-1 | $LiPF_6$ | EC/EMC/DMC | 10 | 10.13 |

The electrolytic solutions of Examples all exhibited ionic conductivities. Thus, the electrolytic solutions of the present invention are all understood to function as electrolytic solutions of various types of power storage devices. In particular, the electrolytic solution of Example 1-5 used, as the organic solvent, only DMC having a relatively low permittivity, but exhibited ionic conductivity substantially equivalent to that of the electrolytic solution of Comparative Example 4-1 which is a representative example of a conventional electrolytic solution that uses EC having a high permittivity. This feature is particularly noteworthy.

Figure 3:
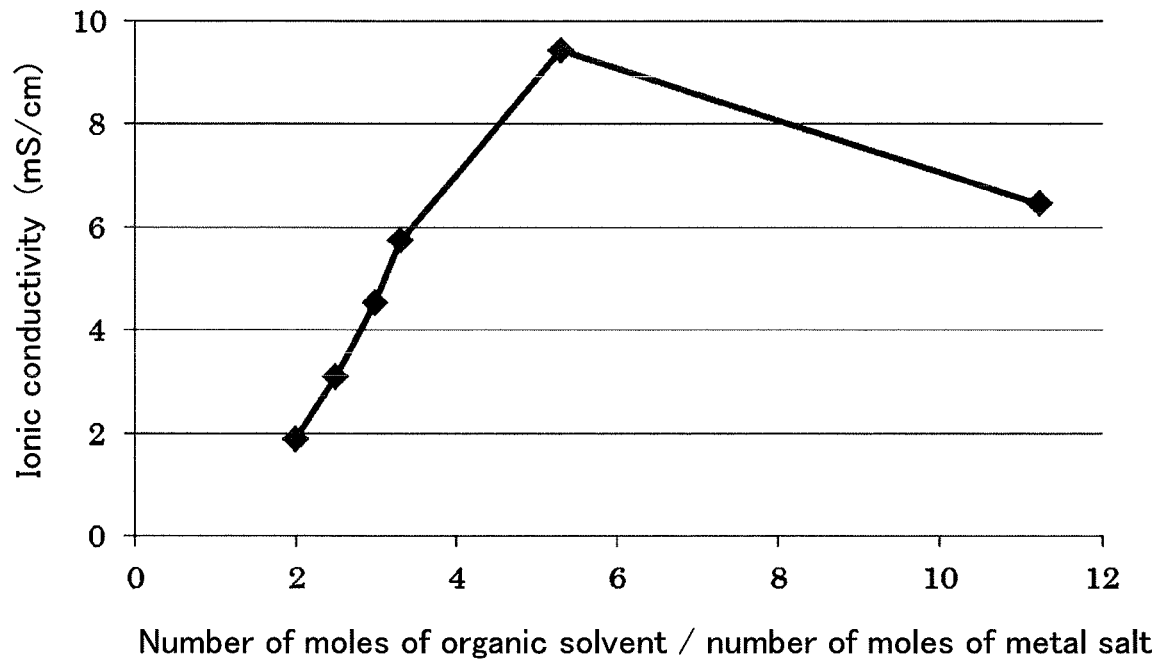
FIG. 3 is a graph showing the relationship between the mole ratio of an organic solvent relative to a metal salt and the ionic conductivity, in each of the electrolytic solutions of Examples 1-1 to 1-5 and Comparative Example 2-1.

Here, with respect to the electrolytic solutions of Examples 1-1 to 1-5 and Comparative Example 2-1, each having $LiPF_6$ as the metal salt and DMC as the organic solvent, a graph showing the relationship between the mole ratio of the organic solvent relative to the metal salt and the ionic conductivity was made. FIG. 3 shows this graph.

Figure 4:
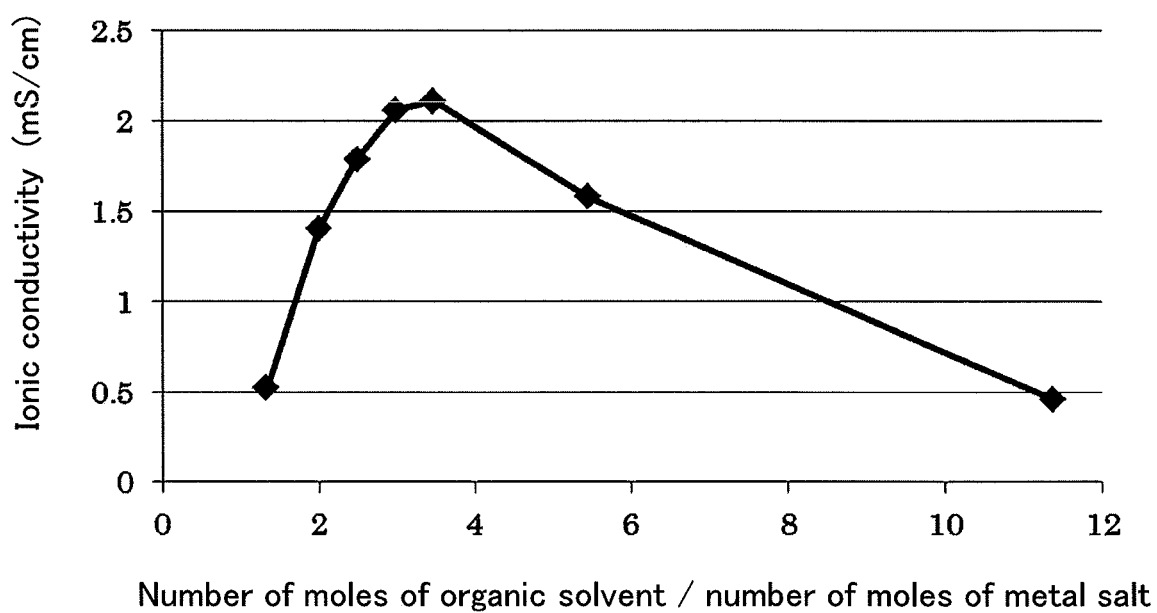
FIG. 4 is a graph showing the relationship between the mole ratio of an organic solvent relative to a metal salt and the ionic conductivity, in each of the electrolytic solutions of Examples 4-1 to 4-6 and Comparative Example 3-1.

In addition, with respect to the electrolytic solutions of Examples 4-1 to 4-6 and Comparative Example 3-1, each having $LiBF_4$ as the metal salt and DMC as the organic solvent, a graph showing the relationship between the mole ratio of the organic solvent relative to the metal salt and the ionic conductivity was made. FIG. 4 shows this graph.

FIG. 3 suggests that, in an electrolytic solution having $LiPF_6$ as the metal salt and DMC as the organic solvent, the local maximum of the ionic conductivity is present at a mole ratio of around 6. Thus, from the viewpoint of ionic conductivity, the electrolytic solution having $LiPF_6$ as the metal salt and DMC as the organic solvent is considered to have a mole ratio preferably in a range of 4 to 8, more preferably in a range of 5 to 7, and further preferably in a range of 5 to 6.

FIG. 4 suggests that, in an electrolytic solution having $LiBF_4$ as the metal salt and DMC as the organic solvent, the local maximum of the ionic conductivity is present at a mole ratio in a range of 3 to 4. Thus, from the viewpoint of ionic conductivity, the electrolytic solution having $LiBF_4$ as the metal salt and DMC as the organic solvent is considered to have a mole ratio preferably in a range of 2 to 6, more preferably in a range of 3 to 5, and further preferably in a range of 3 to 4.

Evaluation Example 2: Density

Densities at 20° C. of the electrolytic solutions of Examples and Comparative Examples were measured. Table 3-1 and Table 3-2 shows the results.

TABLE 3-1

| | Metal salt | Organic solvent | Number of moles of organic solvent/number of moles of metal salt | Density (g/cm³) |
|---|---|---|---|---|
| Example 1-1 | $LiPF_6$ | DMC | 2 | 1.46 |
| Example 1-2 | $LiPF_6$ | DMC | 2.5 | 1.41 |
| Example 1-3 | $LiPF_6$ | DMC | 3 | 1.36 |
| Example 1-4 | $LiPF_6$ | DMC | 3.31 | 1.35 |
| Example 1-5 | $LiPF_6$ | DMC | 5.31 | 1.26 |
| Example 2-1 | $LiPF_6$ | EMC | 2.15 | 1.34 |
| Example 3-1 | $LiPF_6$ | DEC | 2.69 | 1.23 |
| Example 4-1 | $LiBF_4$ | DMC | 1.33 | 1.38 |
| Example 4-2 | $LiBF_4$ | DMC | 2 | 1.30 |
| Example 4-3 | $LiBF_4$ | DMC | 2.5 | 1.27 |
| Example 4-4 | $LiBF_4$ | DMC | 3 | 1.24 |
| Example 4-5 | $LiBF_4$ | DMC | 3.48 | 1.22 |
| Example 4-6 | $LiBF_4$ | DMC | 5.46 | 1.17 |
| Example 5-1 | $LiBF_4$ | EMC | 2 | 1.22 |
| Example 6-1 | $LiBF_4$ | DEC | 2.23 | 1.14 |

TABLE 3-2

| | Metal salt | Organic solvent | Number of moles of organic solvent/number of moles of metal salt | Density (g/cm³) |
|---|---|---|---|---|
| Comparative Example 2-1 | $LiPF_6$ | DMC | 11.24 | 1.16 |
| Comparative Example 3-1 | $LiBF_4$ | DMC | 11.37 | 1.12 |
| Comparative Example 4-1 | $LiPF_6$ | EC/EMC/DMC | 10 | 1.23 |

The above results show that, when the value of the number of moles of organic solvent/number of moles of metal salt in an electrolytic solution decreases, the density of the electrolytic solution increases.

Evaluation Example 3: IR Measurement

Figure 5:
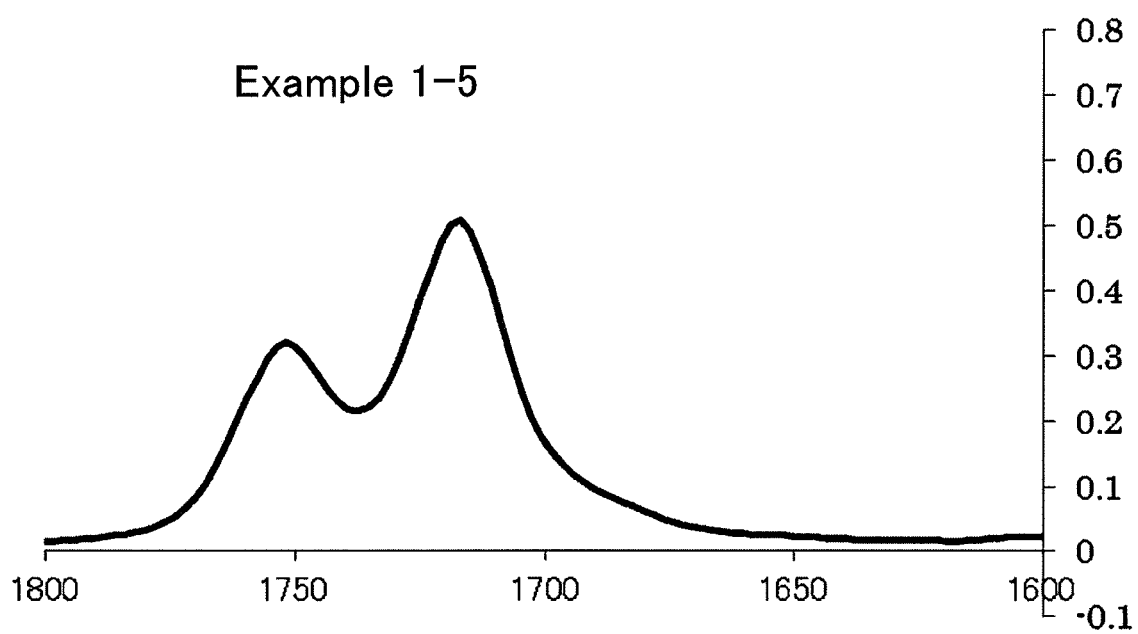
FIG. 5 is an IR spectrum of the electrolytic solution of Example 1-5.
Figure 6:
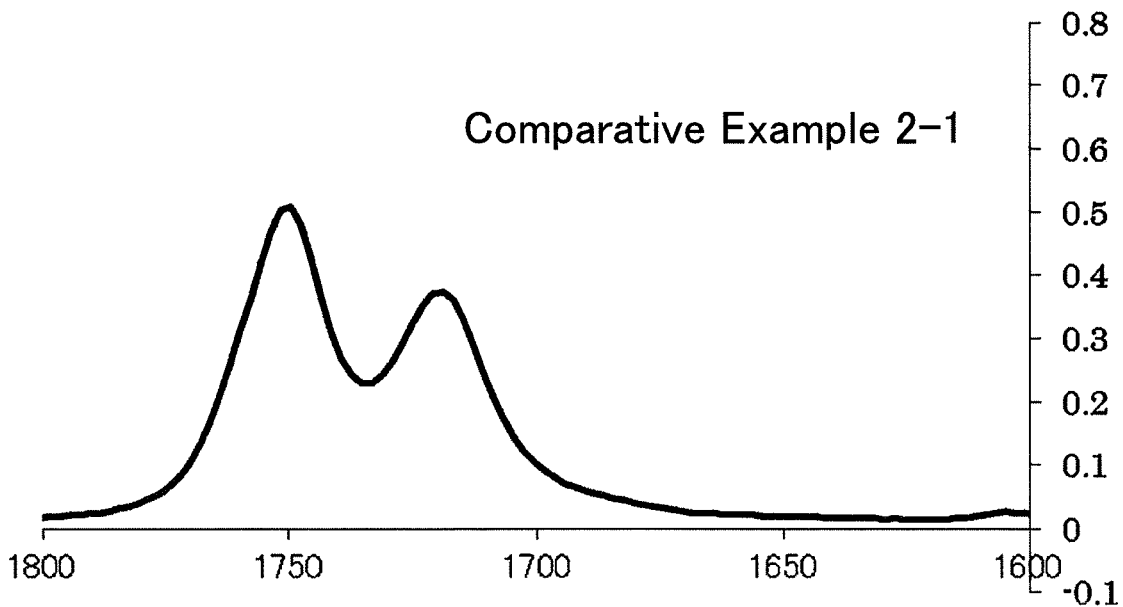
FIG. 6 is an IR spectrum of the electrolytic solution of Comparative Example 2-1.
Figure 7:
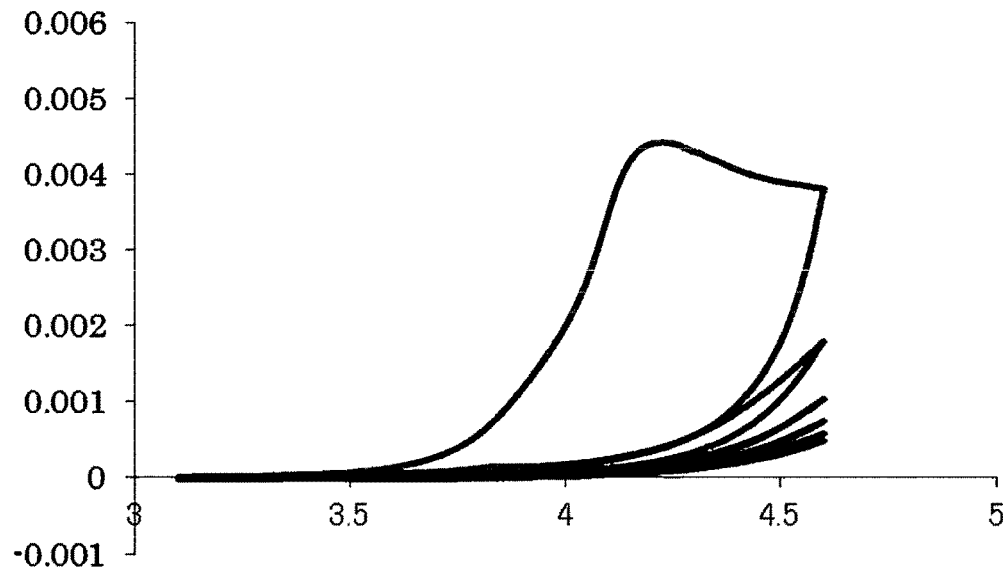
FIG. 7 is a graph of cyclic voltammetry at 3.1 V to 4.6 V performed on a half-cell of Example A-1-5 in Evaluation Example A.
Figure 8:
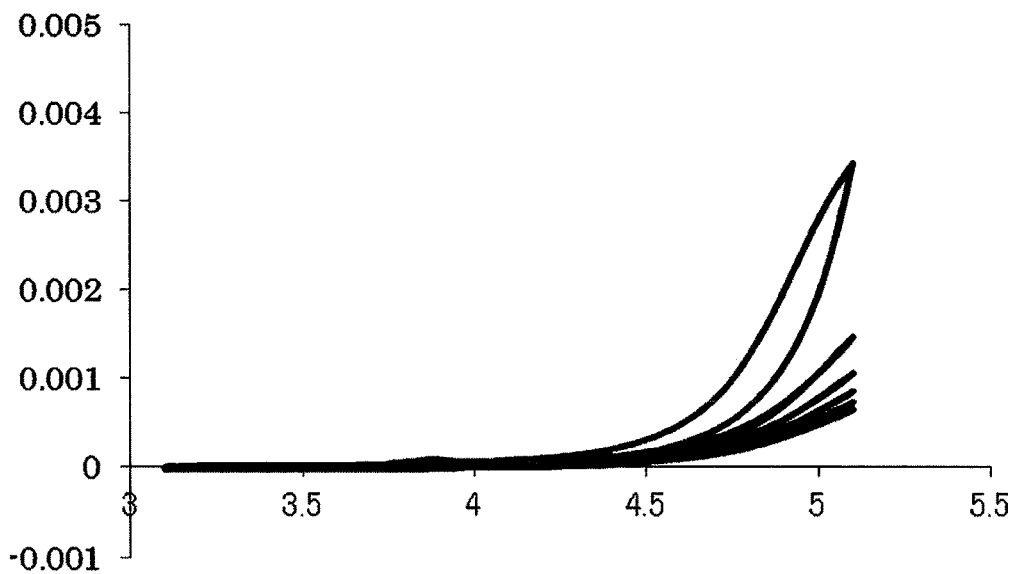
FIG. 8 is a graph of cyclic voltammetry at 3.1 V to 5.1 V performed on the half-cell of Example A-1-5 in Evaluation Example A.
Figure 9:
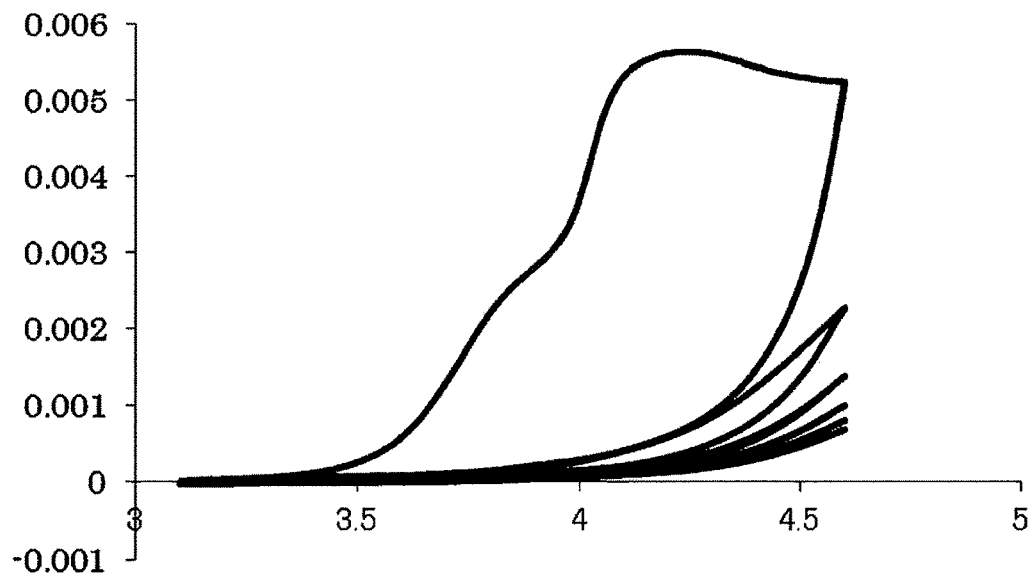
FIG. 9 is a graph of cyclic voltammetry at 3.1 V to 4.6 V performed on a half-cell of Comparative Example A-4-1 in Evaluation Example A.
Figure 10:
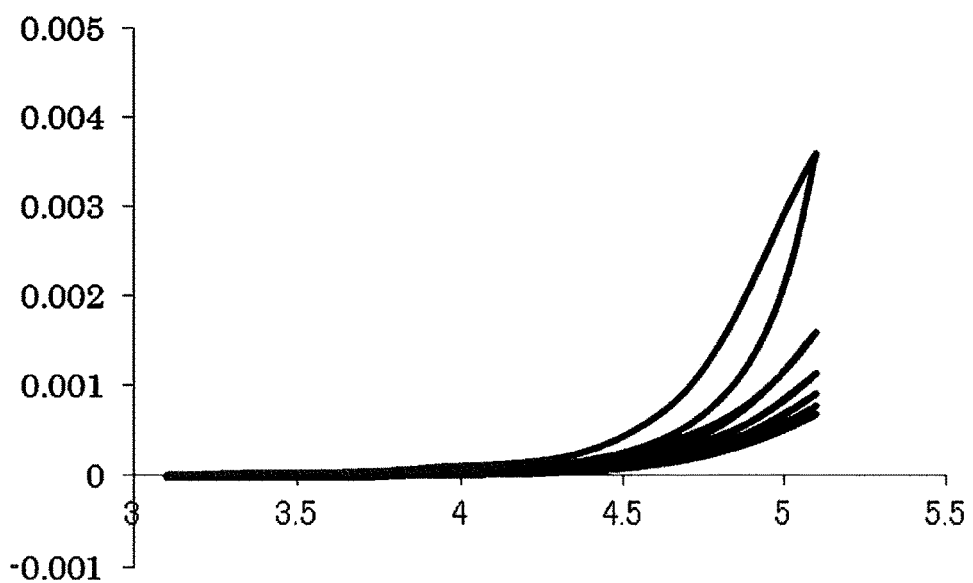
FIG. 10 is a graph of cyclic voltammetry at 3.1 V to 5.1 V performed on the half-cell of Comparative Example A-4-1 in Evaluation Example A.

IR measurement was performed under the following condition on the electrolytic solutions of representative Examples and Comparative Examples. With respect to the electrolytic solution of Example 1-5 and the electrolytic solution of Comparative Example 2-1, the IR spectra in the range of 1600 to 1800 cm$^{-1}$ are shown in FIG. 5 and FIG. 6, respectively. In each figure, the horizontal axis represents wave number (cm$^{-1}$) and the vertical axis represents absorbance (reflective absorbance).

IR measurement condition
Device: FT-IR (manufactured by Bruker Optics K.K.)
Measurement condition: ATR method (diamond was used)
Measurement atmosphere: inert gas atmosphere In the IR spectrum of the electrolytic solution of Example 1-5 shown in FIG. 5, at around 1750 cm$^{-1}$, a shoulder-like peak derived from stretching vibration of the double bond between C and O of DMC was observed at a peak intensity Io of 0.322. Further, in the IR spectrum shown in FIG. 5, at around 1717 cm$^{-1}$ shifted to the lower wave number side from around 1750 cm$^{-1}$, a characteristic peak derived from stretching vibration of the double bond between C and O of DMC was observed at a peak intensity Is of 0.510. The relationship between peak intensities Io and Is was Is>Io.

Io and Is observed in the IR spectrum of each electrolytic solution and the relationship thereof are shown in Table 4-1 and Table 4-2.

TABLE 4-1

| | Metal salt | Organic solvent | Number of moles of organic solvent/number of moles of metal salt | Io and Is |
|---|---|---|---|---|
| Example 1-1 | LiPF$_6$ | DMC | 2 | Io = 0.188<br>Is = 0.495<br>Is > Io |
| Example 1-3 | LiPF$_6$ | DMC | 3 | Io = 0.182<br>Is = 0.560<br>Is > Io |
| Example 1-4 | LiPF$_6$ | DMC | 3.31 | Io = 0.193<br>Is = 0.561<br>Is > Io |
| Example 1-5 | LiPF$_6$ | DMC | 5.31 | Io = 0.322<br>Is = 0.510<br>Is > Io |
| Example 2-1 | LiPF$_6$ | EMC | 2.15 | Io = 0.143<br>Is = 0.487<br>Is > Io |
| Example 3-1 | LiPF$_6$ | DEC | 2.69 | Io = 0.130<br>Is = 0.474<br>Is > Io |
| Example 4-1 | LiBF$_4$ | DMC | 1.33 | Io = 0.236<br>Is = 0.396<br>Is > Io |
| Example 4-2 | LiBF$_4$ | DMC | 2 | Io = 0.242<br>Is = 0.427<br>Is > Io |
| Example 4-4 | LiBF$_4$ | DMC | 3 | Io = 0.329<br>Is = 0.434<br>Is > Io |
| Example 4-5 | LiBF$_4$ | DMC | 3.48 | Io = 0.370<br>Is = 0.421<br>Is > Io |
| Example 5-1 | LiBF$_4$ | EMC | 2 | Io = 0.240<br>Is = 0.387<br>Is > Io |

TABLE 4-1-continued

| | Metal salt | Organic solvent | Number of moles of organic solvent/number of moles of metal salt | Io and Is |
|---|---|---|---|---|
| Example 6-1 | LiBF$_4$ | DEC | 2.23 | Io = 0.255<br>Is = 0.343<br>Is > Io |

TABLE 4-2

| | Metal salt | Organic solvent | Number of moles of organic solvent/number of moles of metal salt | Io and Is |
|---|---|---|---|---|
| Comparative Example 2-1 | LiPF$_6$ | DMC | 11.24 | Io = 0.508<br>Is = 0.374<br>Io > Is |
| Comparative Example 3-1 | LiBF$_4$ | DMC | 11.37 | Io = 0.580<br>Is = 0.300<br>Io > Is |

The results of Example 1-1, Example 1-3 to Example 1-5, and Comparative Example 2-1, and the results of Example 4-1, Example 4-2, Example 4-4, Example 4-5, and Comparative Example 3-1 indicate that the value of Io tends to increase and the value of Is tends to decrease in accordance with increase in the value of the number of moles of organic solvent/number of moles of metal salt. This phenomenon means that the amount of the organic solvent not coordinated with the metal salt increases in accordance with increase in the value of the number of moles of organic solvent/number of moles of metal salt.

Most of the specific organic solvent contained in the electrolytic solution of the present invention was confirmed to be coordinated with the metal salt.

Evaluation Example 4: Low Temperature Storage Test

Each of the electrolytic solutions of Examples was placed in a container, and the container was filled with inert gas and sealed. These were stored in a −20° C. freezer for two days. After the storage, each container was tilted to observe the fluidity of the electrolytic solution. Table 5-1 shows the results. Each blank in the tables means that measurement was not performed.

TABLE 5-1

| | Metal salt | Organic solvent | Number of moles of organic solvent/number of moles of metal salt | State after storage |
|---|---|---|---|---|
| Example 1-1 | LiPF$_6$ | DMC | 2 | fluidized |
| Example 1-2 | LiPF$_6$ | DMC | 2.5 | fluidized |
| Example 1-3 | LiPF$_6$ | DMC | 3 | fluidized |
| Example 1-4 | LiPF$_6$ | DMC | 3.31 | fluidized |
| Example 1-5 | LiPF$_6$ | DMC | 5.31 | solidified |
| Example 2-1 | LiPF$_6$ | EMC | 2.15 | fluidized |
| Example 3-1 | LiPF$_6$ | DEC | 2.69 | solidified |

TABLE 5-1-continued

|  | Metal salt | Organic solvent | Number of moles of organic solvent/number of moles of metal salt | State after storage |
|---|---|---|---|---|
| Example 4-1 | LiBF$_4$ | DMC | 1.33 | fluidized |
| Example 4-2 | LiBF$_4$ | DMC | 2 |  |
| Example 4-3 | LiBF$_4$ | DMC | 2.5 |  |
| Example 4-4 | LiBF$_4$ | DMC | 3 | solidified |
| Example 4-5 | LiBF$_4$ | DMC | 3.48 | solidified |
| Example 4-6 | LiBF$_4$ | DMC | 5.46 | solidified |
| Example 5-1 | LiBF$_4$ | EMC | 2 | fluidized |
| Example 6-1 | LiBF$_4$ | DEC | 2.23 | solidified |

The results of Example 1-1 to Example 1-5 and the like show that solidification at a low temperature is more likely to occur in accordance with increase in the value of the mole ratio of the organic solvent to the metal salt, i.e., as the value thereof becomes closer to conventional values. In addition, from the results of Example 1-3 and Example 4-4 and the like, the electrolytic solution having LiPF$_6$ as the metal salt is considered to be excellent in low temperature fluidity compared to the electrolytic solution having LiBF$_4$ as the metal salt. Further, when results of the electrolytic solutions having similar levels of mole ratios of Examples 1-1 to 1-3, 2-1, 3-1, and the like are compared to one another, the low temperature fluidity of each of the electrolytic solutions having DMC and EMC as the solvent is considered to be excellent compared to the low temperature fluidity of the electrolytic solution having DEC as the solvent.

Example A-1-1

A half-cell using the electrolytic solution of Example 1-1 was produced in the following manner.
An aluminum foil (JIS A1000 SERIES) having a diameter of 13.82 mm, an area of 1.5 cm$^2$, and a thickness of 15 μm was used as the working electrode, and metal Li was used as the counter electrode. As the separator, a glass fiber filter (GE Healthcare Japan Corp., model 1825-055, Whatman glass fiber filter, thickness 400 μm) was used.
The working electrode, the counter electrode, the separator, and the electrolytic solution of Example 1-1 were housed in a battery case (Hohsen Corp., CR2032 type coin cell case) to form a half-cell. The obtained half-cell was used as the half-cell of Example A-1-1.

Example A-1-2

A half-cell of Example A-1-2 was produced by a method similar to that in Example A-1-1, except for using the electrolytic solution of Example 1-2.

Example A-1-3

A half-cell of Example A-1-3 was produced by a method similar to that in Example A-1-1, except for using the electrolytic solution of Example 1-3.

Example A-1-5

A half-cell of Example A-1-5 was produced by a method similar to that in Example A-1-1, except for using the electrolytic solution of Example 1-5.

Example A-2-1

A half-cell of Example A-2-1 was produced by a method similar to that in Example A-1-1, except for using the electrolytic solution of Example 2-1.

Example A-3-1

A half-cell of Example A-3-1 was produced by a method similar to that in Example A-1-1, except for using the electrolytic solution of Example 3-1.

Example A-4-1

A half-cell of Example A-4-1 was produced by a method similar to that in Example A-1-1, except for using the electrolytic solution of Example 4-1.

Example A-4-3

A half-cell of Example A-4-3 was produced by a method similar to that in Example A-1-1, except for using the electrolytic solution of Example 4-3.

Example A-4-4

A half-cell of Example A-4-4 was produced by a method similar to that in Example A-1-1, except for using the electrolytic solution of Example 4-4.

Example A-4-6

A half-cell of Example A-4-6 was produced by a method similar to that in Example A-1-1, except for using the electrolytic solution of Example 4-6.

Example A-5-1

A half-cell of Example A-5-1 was produced by a method similar to that in Example A-1-1, except for using the electrolytic solution of Example 5-1.

Example A-6-1

A half-cell of Example A-6-1 was produced by a method similar to that in Example A-1-1, except for using the electrolytic solution of Example 6-1.

Comparative Example A-2-1

A half-cell of Comparative Example A-2-1 was produced by a method similar to that in Example A-1-1, except for using the electrolytic solution of Comparative Example 2-1.

Comparative Example A-4-1

A half-cell of Comparative Example A-4-1 was produced by a method similar to that in Example A-1-1, except for using the electrolytic solution of Comparative Example 4-1.

Evaluation Example A: Cyclic Voltammetry Evaluation Using Working Electrode A1

With respect to the half-cells of Examples and Comparative Examples above, 6 cycles of cyclic voltammetry evaluation were performed under a condition of 3.1 V to 4.6 V and 1 mV/s, and then successively, 6 cycles of cyclic voltammetry evaluation were performed under a condition of 3.1 V to 5.1 V and 1 mV/s. FIG. 7 to FIG. 10 show graphs showing the relationship between potential and response current in the half-cells of Example A-1-5 and Comparative Example A-4-1. In each figure, the horizontal axis represents potential (V), and the vertical axis represents response current (mA). Table 6 shows the maximum current value observed while the voltage was increased at the 6th cycle under each condition.

TABLE 6

| Half-cell | Metal salt | Organic solvent | Number of moles of organic solvent/number of moles of metal salt | Maximum current value (mA) Upper: 3.1-4.6 V Lower: 3.1-5.1 V |
|---|---|---|---|---|
| Example A-1-1 | $LiPF_6$ | DMC | 2 | 0.000320 0.000293 |
| Example A-1-2 | $LiPF_6$ | DMC | 2.5 | 0.000364 0.000263 |
| Example A-1-3 | $LiPF_6$ | DMC | 3 | 0.000451 0.000338 |
| Example A-1-5 | $LiPF_6$ | DMC | 5.31 | 0.000491 0.000655 |
| Example A-2-1 | $LiPF_6$ | EMC | 2.15 | 0.000370 0.000337 |
| Example A-3-1 | $LiPF_6$ | DEC | 2.69 | 0.000339 0.000742 |
| Example A-4-1 | $LiBF_4$ | DMC | 1.33 | 0.000498 0.000615 |
| Example A-4-3 | $LiBF_4$ | DMC | 2.5 | 0.000379 0.000368 |
| Example A-4-4 | $LiBF_4$ | DMC | 3 | 0.000590 0.000818 |
| Example A-4-6 | $LiBF_4$ | DMC | 5.46 | 0.000447 0.000670 |
| Example A-5-1 | $LiBF_4$ | EMC | 2 | 0.000388 0.000295 |
| Example A-6-1 | $LiBF_4$ | DEC | 2.23 | 0.000335 0.000228 |
| Comparative Example A-2-1 | $LiPF_6$ | DMC | 11.24 | 0.000924 0.001352 |
| Comparative Example A-4-1 | $LiPF_6$ | EC/EMC/DMC | 10 | 0.000696 0.000684 |

In Evaluation Example A, oxidation current resulting from corrosion of aluminum serving as the working electrode and oxidative destruction of the electrolytic solution is estimated to be observed as increase in the current value. In each of the half-cells of Examples and Comparative Examples above, the current value decreased in accordance with increase in the number of cycles. From the results in Table 6, the half-cells using the electrolytic solution of the present invention are each considered to have exhibited a current value substantially equivalent to that of conventional half-cells using EC-containing electrolytic solutions. In particular, in the cycle at 3.1 V to 4.6 V, the half-cells using the electrolytic solution of the present invention each exhibited a lower current value than the half-cells of Comparative Examples. Further, the half-cells of Example A-1-1, Example A-1-2, Example A-1-3, Example A-2-1, Example A-4-3, Example A-5-1, and Example A-6-leach exhibited a significantly lower current value than the half-cells of Comparative Examples, at each voltage. In addition, the half-cells using the electrolytic solution of the present invention are each considered to have exhibited a smaller current value than the half-cell using the electrolytic solution of Comparative Example 2-1 having a large value of the number of moles of organic solvent/number of moles of metal salt. That the electrolytic solution of the present invention does not undergo significant oxidative destruction even at a high potential of 4.6 V, has low corrosiveness to aluminum, and suppresses aluminum oxidation is suggested. In addition, a stable coating being formed on the aluminum foil by the electrolytic solution of the present invention is suggested. The electrolytic solution of the present invention is considered to serve as a suitable electrolytic solution for power storage devices using aluminum as the current collector or the like.

Example B-1-1

A lithium ion secondary battery of Example B-1-1 using the electrolytic solution of Example 1-1 was produced in the following manner.

94 parts by mass of $LiNi_{0.5}Co_{0.3}Mn_{0.2}O_2$ having a layered rock salt structure serving as the active material, 3 parts by mass of acetylene black serving as the conductive additive, and 3 parts by mass of polyvinylidene fluoride serving as the binding agent were mixed together. This mixture was dispersed in a proper amount of N-methyl-2-pyrrolidone to make a slurry. As the current collector, an aluminum foil having a thickness of 15 μm was prepared. The slurry was applied in a film form on a surface of the aluminum foil by using a doctor blade. The aluminum foil on which the slurry was applied was dried for 20 minutes at 80° C. to remove N-methyl-2-pyrrolidone through volatilization. Then, this aluminum foil was pressed to obtain a joined object. The obtained joined object was heated and dried in a vacuum dryer for 6 hours at 120° C. to obtain an aluminum foil having an active material layer formed thereon. This aluminum foil having an active material layer formed thereon was used as the working electrode.

Metal Li was used as the counter electrode. As the separator, a glass fiber filter (GE Healthcare Japan Corp., model 1825-055, Whatman glass fiber filter, thickness 400 μm) was used.

The working electrode, the counter electrode, the separator interposed between the electrodes, and the electrolytic solution of Example 1-1 were housed in a battery case (Hohsen Corp., CR2032 type coin cell case), to form a half-cell. The obtained half-cell was used as the lithium ion secondary battery of Example B-1-1.

Example B-1-3

A lithium ion secondary battery of Example B-1-3 was produced by a method similar to that in Example B-1-1, except for using the electrolytic solution of Example 1-3.

Example B-1-5

A lithium ion secondary battery of Example B-1-5 was produced by a method similar to that in Example B-1-1, except for using the electrolytic solution of Example 1-5.

Example B-2-1

A lithium ion secondary battery of Example B-2-1 was produced by a method similar to that in Example B-1-1, except for using the electrolytic solution of Example 2-1.

Example B-3-1

A lithium ion secondary battery of Example B-3-1 was produced by a method similar to that in Example B-1-1, except for using the electrolytic solution of Example 3-1.

Example B-4-1

A lithium ion secondary battery of Example B-4-1 was produced by a method similar to that in Example B-1-1, except for using the electrolytic solution of Example 4-1.

Example B-4-2

A lithium ion secondary battery of Example B-4-2 was produced by a method similar to that in Example B-1-1, except for using the electrolytic solution of Example 4-2.

Example B-4-4

A lithium ion secondary battery of Example B-4-4 was produced by a method similar to that in Example B-1-1, except for using the electrolytic solution of Example 4-4.

Example B-4-6

A lithium ion secondary battery of Example B-4-6 was produced by a method similar to that in Example B-1-1, except for using the electrolytic solution of Example 4-6.

Comparative Example B-2-1

A lithium ion secondary battery of Comparative Example B-2-1 was produced by a method similar to that in Example B-1-1, except for using the electrolytic solution of Comparative Example 2-1.

Comparative Example B-3-1

A lithium ion secondary battery of Comparative Example B-3-1 was produced by a method similar to that in Example B-1-1, except for using the electrolytic solution of Comparative Example 3-1.

Comparative Example B-4-1

A lithium ion secondary battery of Comparative Example B-4-1 was produced by a method similar to that in Example B-1-1, except for using the electrolytic solution of Comparative Example 4-1.

Evaluation Example B-1

For each of the lithium ion secondary batteries, a 3.1 V-4.2 V charging and discharging cycle of constant current charging up to voltage 4.2 V and constant current discharging down to voltage 3.1 V was performed by 10 cycles at a condition of 25° C. and 0.5 C rate. Table 7 shows the results of initial discharge capacity, initial efficiency calculated by (initial discharge capacity)/(initial charge capacity), and capacity retention rate calculated by (discharge capacity after 10 cycles)/(initial discharge capacity). In the description here, the counter electrode is regarded as the negative electrode, and the working electrode is regarded as the positive electrode.

TABLE 7

| | Metal salt of electrolytic solution, Organic solvent, Number of moles of organic solvent/number of moles of metal salt | Initial discharge capacity (mAh) | Initial efficiency | Capacity retention rate |
|---|---|---|---|---|
| Example B-1-1 | $LiPF_6$, DMC 2 | 1.094 | 0.855 | 1.016 |
| Example B-1-3 | $LiPF_6$, DMC 3 | 1.105 | 0.861 | 1.010 |
| Example B-1-5 | $LiPF_6$, DMC 5.31 | 1.106 | 0.848 | 1.015 |
| Example B-2-1 | $LiPF_6$, EMC 2.15 | 1.063 | 0.834 | 1.028 |
| Example B-3-1 | $LiPF_6$, DEC 2.69 | 0.795 | 0.708 | 0.862 |
| Example B-4-1 | $LiBF_4$, DMC 1.33 | 1.112 | 0.865 | 1.011 |
| Example B-4-2 | $LiBF_4$, DMC 2 | 1.131 | 0.868 | 1.009 |
| Example B-4-4 | $LiBF_4$, DMC 3 | 1.135 | 0.868 | 1.013 |
| Example B-4-6 | $LiBF_4$, DMC 5.46 | 1.118 | 0.858 | 1.017 |
| Comparative Example B-2-1 | $LiPF_6$, DMC 11.24 | 1.099 | 0.850 | 1.008 |
| Comparative Example B-3-1 | $LiBF_4$, DMC 11.37 | 1.064 | 0.846 | 0.960 |
| Comparative Example B-4-1 | $LiPF_6$, EC/EMC/DMC 10 | 1.116 | 0.847 | 1.001 |

From the results above, the secondary batteries provided with the electrolytic solution of the present invention and the positive electrode active material having a layered rock salt structure were confirmed to be reversibly charged and discharged. In particular, with respect to the secondary batteries provided with the electrolytic solution of the present invention having DMC, the initial discharge capacity, the initial efficiency, and the capacity retention rate were all equivalent to or higher than those of the secondary batteries provided with conventional electrolytic solutions.

From the result indicating that lithium ion secondary batteries of Examples above were reversibly charged and discharged, the electrolytic solution of the present invention is considered to reversibly react with the positive electrode active material and the polarized electrode material that act in adsorption/desorption or insertion/extraction of lithium to/from the lithium site similarly to the active material having a layered rock salt structure. Most of the above-described specific positive electrode active material and polarized material are presumed to correspond to such an active material.

Evaluation Example B-2

With respect to each of the lithium ion secondary batteries of Example B-1-5, Comparative Example B-2-1, and Comparative Example B-4-1, a charging and discharging cycle test was performed in which charging from 3.1 V to 4.2 V and discharging from 4.2 V to 3.1 V were performed at room temperature in the rate order of 0.1 C, 0.2 C, 0.5 C, 1 C, 2 C, 5 C, and 10 C, three times for each rate. Table 8 shows the results obtained by calculating the ratio of the discharge capacity at each rate relative to the discharge capacity at 0.1 C rate. In the description here, the counter electrode is regarded as the negative electrode and the working electrode is regarded as the positive electrode. "1 C" refers to the value of a current required for fully charging or discharging a battery in 1 hour under a constant current.

TABLE 8

|  | Example B-1-5 | Comparative Example B-2-1 | Comparative Example B-4-1 |
|---|---|---|---|
|  | Metal salt of electrolytic solution | | |
|  | $LiPF_6$ | $LiPF_6$ | $LiPF_6$ |
|  | Organic solvent | | |
|  | DMC | DMC | EC/EMC/DMC |
|  | Number of moles of organic solvent/number of moles of metal salt | | |
|  | 5.31 | 11.24 | 10 |
| 0.2C/0.1C | 1.009 | 1.010 | 0.980 |
| 0.5C/0.1C | 0.981 | 0.976 | 0.943 |
| 1C/0.1C | 0.949 | 0.938 | 0.907 |
| 2C/0.1C | 0.910 | 0.891 | 0.856 |
| 5C/0.1C | 0.832 | 0.796 | 0.773 |
| 10C/0.1C | 0.702 | 0.653 | 0.656 |

With reference to the result shown in Table 8, the lithium ion secondary battery of Example B-1-5 had smaller decrease in the capacity at each rate than the lithium ion secondary battery of each Comparative Example, and exhibited excellent rate characteristics. The secondary batteries provided with the electrolytic solution of the present invention and the positive electrode active material having a layered rock salt structure were confirmed to exhibit excellent rate characteristics.

Example C-1-1

A lithium ion secondary battery of Example C-1-1 using the electrolytic solution of Example 1-1 was produced in the following manner.

98 parts by mass of a natural graphite serving as the active material, and 1 part by mass of styrene butadiene rubber and 1 part by mass of carboxymethyl cellulose, which both served as the binding agent, were mixed together. This mixture was dispersed in a proper amount of ion exchanged water to make a slurry. As the current collector, a copper foil having a thickness of 20 μm was prepared. The slurry was applied in a film form on a surface of this copper foil by using a doctor blade. The copper foil on which the slurry was applied was dried to remove water, and then, the copper foil was pressed to obtain a joined object. The obtained joined object was heated and dried in a vacuum dryer for 6 hours at 100° C. to obtain a copper foil having an active material layer formed thereon. This copper foil having an active material layer formed thereon was used as the working electrode.

Metal Li was used as the counter electrode. As the separator, a glass fiber filter (GE Healthcare Japan Corp., model 1825-055, Whatman glass fiber filter, thickness 400 μm) was used.

The working electrode, the counter electrode, the separator interposed between the electrodes, and the electrolytic solution of Example 1-1 were housed in a battery case (Hohsen Corp., CR2032 type coin cell case), to form a half-cell. The obtained half-cell was used as the lithium ion secondary battery of Example C-1-1.

Example C-1-3

A lithium ion secondary battery of Example C-1-3 was produced by a method similar to that in Example C-1-1, except for using the electrolytic solution of Example 1-3.

Example C-1-5

A lithium ion secondary battery of Example C-1-5 was produced by a method similar to that in Example C-1-1, except for using the electrolytic solution of Example 1-5.

Example C-2-1

A lithium ion secondary battery of Example C-2-1 was produced by a method similar to that in Example C-1-1, except for using the electrolytic solution of Example 2-1.

Example C-3-1

A lithium ion secondary battery of Example C-3-1 was produced by a method similar to that in Example C-1-1, except for using the electrolytic solution of Example 3-1.

Example C-4-4

A lithium ion secondary battery of Example C-4-4 was produced by a method similar to that in Example C-1-1, except for using the electrolytic solution of Example 4-4.

Comparative Example C-2-1

A lithium ion secondary battery of Comparative Example C-2-1 was produced by a method similar to that in Example C-1-1, except for using the electrolytic solution of Comparative Example 2-1.

Comparative Example C-4-1

A lithium ion secondary battery of Comparative Example C-4-1 was produced by a method similar to that in Example C-1-1, except for using the electrolytic solution of Comparative Example 4-1.

Evaluation Example C-1

For each of the lithium ion secondary batteries, a 2.0 V-0.01 V charging and discharging cycle of constant current discharging to voltage 2.0 V and constant current charging to voltage 0.01 V was performed by 10 cycles at a condition of 25° C. and 0.5 C rate. Table 9 shows the results of initial discharge capacity, initial efficiency calculated by (initial charge capacity)/(initial discharge capacity), and capacity retention rate calculated by (discharge capacity after 10 cycles)/(initial discharge capacity). In the description here, the counter electrode is regarded as the positive electrode, and the working electrode is regarded as the negative electrode.

TABLE 9

| | Metal salt of electrolytic solution, Organic solvent Number of moles of organic solvent/number of moles of metal salt | Initial discharge capacity (mAh) | Initial efficiency | Capacity retention rate |
|---|---|---|---|---|
| Example C-1-1 | LiPF$_6$, DMC 2 | 0.976 | 0.845 | 1.066 |
| Example C-1-3 | LiPF$_6$, DMC 3 | 1.941 | 0.932 | 1.023 |
| Example C-1-5 | LiPF$_6$, DMC 5.31 | 2.089 | 0.923 | 0.983 |
| Example C-2-1 | LiPF$_6$, EMC 2.15 | 0.961 | 0.812 | 0.465 |
| Example C-3-1 | LiPF$_6$, DEC 2.69 | 0.396 | 0.631 | 1.106 |
| Example C-4-4 | LiBF$_4$, DMC 3 | 1.811 | 0.745 | 0.410 |
| Comparative Example C-2-1 | LiPF$_6$, DMC 11.24 | 2.083 | 0.926 | 0.975 |
| Comparative Example C-4-1 | LiPF$_6$, EC/EMC/DMC 10 | 2.111 | 0.949 | 0.989 |

From the result above, the secondary batteries provided with the electrolytic solution of the present invention and the graphite were confirmed to be reversibly charged and discharged. In particular, in each of the lithium ion secondary batteries of Example C-1-3 and Example C-1-5, the initial discharge capacity, the initial efficiency, and the capacity retention rate were in good balance and at good levels. From this result, among the electrolytic solutions of the present invention, electrolytic solutions that each have LiPF$_6$ as the metal salt, DMC as the organic solvent, and the number of moles of organic solvent/number of moles of metal salt being about 2.5-8, more suitably 4-8, are considered to suitably reversibly react with the negative electrode provided with the graphite.

According to conventional technical common knowledge, in order to perform reversibly charging and discharging with respect to a negative electrode provided with a graphite, an electrolytic solution having a cyclic carbonate such as EC has been considered to be indispensable. However, as shown by the results above, with the electrolytic solution of the present invention, reversible charging and discharging is realized with respect to the negative electrode provided with a graphite. In addition, among the electrolytic solutions of the present invention, electrolytic solutions that each have LiPF$_6$ as the metal salt, DMC as the organic solvent, and the number of moles of organic solvent/number of moles of metal salt being about 2.5-8 were demonstrated to exhibit charging and discharging characteristics substantially equivalent to those of conventional EC-containing electrolytic solutions.

As described above, the electrolytic solution of the present invention realizes reversible lithium adsorption/desorption reaction with respect to the graphite that readily reduces and degrades the electrolytic solution due to a very low potential, i.e. 0 V (vs Li/Li+), reached during Li occlusion. Therefore, the electrolytic solution of the present invention is considered to reversibly react, also with respect to a polarized material such as active carbon or the negative electrode active material that has a higher lithium adsorption/desorption reaction potential than the graphite and that is less likely to reduce and degrade the electrolytic solution.

Figure 11:
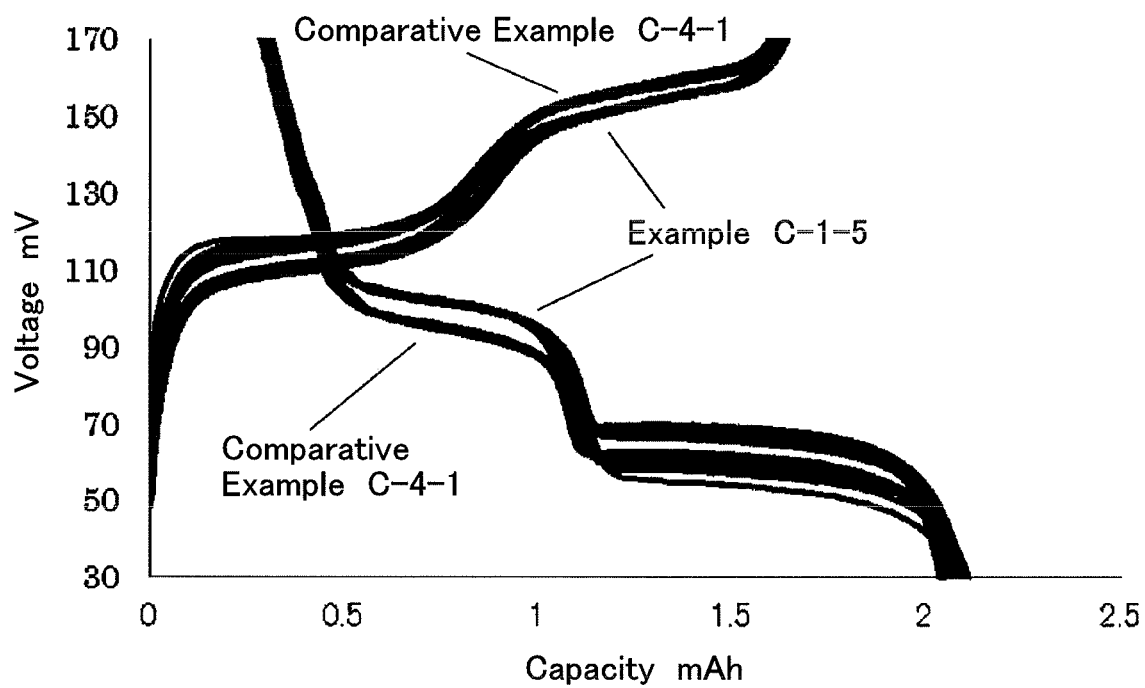
FIG. 11 shows, in an overlaid manner, enlarged charging and discharging curves of a lithium ion secondary battery of Example C-1-5 and enlarged charging and discharging curves of a lithium ion secondary battery of Comparative Example C-4-1, in Evaluation Example C-1.

FIG. 11 shows, in an overlaid manner, enlarged charging and discharging curves of the lithium ion secondary battery of Example C-1-5 and enlarged charging and discharging curves of the lithium ion secondary battery of Comparative Example C-4-1, the curves having been obtained during the second cycle and thereafter in Evaluation Example C-1.

When the charging and discharging curves shown in FIG. 11 are compared to each other, the curves of Example C-1-5 during charging are at higher potentials and the curves of Example C-1-5 during discharging are at lower potentials. This phenomenon is speculated to mean that the magnitude of polarization degree in the lithium ion secondary battery of Example C-1-5 is small.

Evaluation Example C-2

With respect to each of the lithium ion secondary batteries of Example C-1-5, Comparative Example C-2-1, and Comparative Example C-4-1, a charging and discharging cycle test was performed in which discharging from 0.01 V to 2 V and charging from 2 V to 0.01 V were performed at room temperature in the rate order of 0.1 C, 0.2 C, 0.5 C, 1 C, 2 C, 5 C, and 10 C, three times for each rate. Table 10 shows the results obtained by calculating the ratio of the discharge capacity at each rate relative to the discharge capacity at 0.1 C rate. In the description here, the counter electrode is regarded as the positive electrode, and the working electrode is regarded as the negative electrode.

TABLE 10

| | Example C-1-5 | Comparative Example C-2-1 | Comparative Example C-4-1 |
|---|---|---|---|
| Metal salt of electrolytic solution, | | | |
| | LiPF$_6$ | LiPF$_6$ | LiPF$_6$ |
| Organic solvent, | | | |
| | DMC | DMC | EC/EMC/DMC |
| Number of moles of organic solvent/number of moles of metal salt | | | |
| | 5.31 | 11.24 | 10 |
| 0.2C/0.1C | 0.969 | 0.955 | 0.962 |
| 0.5C/0.1C | 0.926 | 0.885 | 0.888 |
| 1C/0.1C | 0.861 | 0.773 | 0.430 |
| 2C/0.1C | 0.446 | 0.356 | 0.126 |
| 5C/0.1C | 0.107 | 0.062 | 0.028 |
| 10C/0.1C | 0.034 | 0.020 | 0.011 |

With reference to the results shown in Table 10, the lithium ion secondary battery of Example C-1-5 had smaller decrease in the capacity at each rate than the lithium ion secondary battery of each Comparative Example, and exhibited excellent rate characteristics.

Further, when the result regarding the magnitudes of polarization in Evaluation Example C-1 and the result of Evaluation Example C-2 are taken into consideration, each of the secondary batteries provided with a graphite and provided with, among the electrolytic solutions of the present invention, an electrolytic solution that has LiPF$_6$ as the metal salt, DMC as the organic solvent, and the number of moles of organic solvent/number of moles of metal salt being about 2.5-8, more preferably, 4-8, is considered to have exhibited excellent rate characteristics due to a small degree of polarization.

Example D-1-5

A lithium ion secondary battery of Example D-1-5 using the electrolytic solution of Example 1-5 was produced in the following manner.

90 parts by mass of $Li_{1.1}Ni_{5/10}Co_{3/10}Mn_{2/10}O_2$ serving as the positive electrode active material, 8 parts by mass of acetylene black serving as the conductive additive, and 2 parts by mass of polyvinylidene fluoride serving as the binding agent were mixed together. This mixture was dispersed in a proper amount of N-methyl-2-pyrrolidone to make a slurry. As the positive electrode current collector, an aluminum foil having a thickness of 15 μm and corresponding to JIS A1000 series was prepared. The slurry was applied in a film form on a surface of this aluminum foil by using a doctor blade. The aluminum foil on which the slurry was applied was dried for 20 minutes at 80° C. to remove N-methyl-2-pyrrolidone. Then, this aluminum foil was pressed to obtain a joined object. The obtained joined object was heated and dried in a vacuum dryer for 6 hours at 120° C. to obtain an aluminum foil having a positive electrode active material layer formed thereon. This aluminum foil having a positive electrode active material layer formed thereon was used as the positive electrode. The positive electrode active material layer was formed at 6 mg/cm² per unit area of the applied surface of the positive electrode current collector. The density of the positive electrode active material layer was 2.5 g/cm³.

98 parts by mass of spheroidal graphite as the negative electrode active material, and 1 part by mass of styrene butadiene rubber and 1 part by mass of carboxymethyl cellulose, which both served as the binding agent, were mixed together. This mixture was dispersed in a proper amount of ion exchanged water to make a slurry. As the negative electrode current collector, a copper foil having a thickness of 10 μm was prepared. The slurry was applied in a film form on a surface of the copper foil by using a doctor blade. The copper foil on which the slurry was applied was dried to remove water, and then, the copper foil was pressed to obtain a joined object. The obtained joined object was heated and dried in a vacuum dryer for 6 hours at 100° C. to obtain a copper foil having a negative electrode active material layer formed thereon. This copper foil having a negative electrode active material layer formed thereon was used as the negative electrode. The negative electrode active material layer was formed at 4 mg/cm² per unit area of the applied surface of the negative electrode current collector. The density of the negative electrode active material layer was 1.1 g/cm³.

As the separator, a porous film made from polypropylene and having a thickness of 20 μm was prepared. An electrode assembly was formed by sandwiching the separator between the positive electrode and the negative electrode. The electrode assembly was covered with a set of two sheets of a laminate film. The laminate film was formed into a bag-like shape by having three sides thereof sealed, and the electrolytic solution of Example 1-5 was poured into the laminate film. Four sides were airtight sealed by sealing the remaining one side to obtain a lithium ion secondary battery in which the electrode assembly and the electrolytic solution were sealed. The obtained lithium ion secondary battery was used as the lithium ion secondary battery of Example D-1-5.

Example D-1-6

A lithium ion secondary battery of Example D-1-6 was produced by a method similar to that in Example D-1-5, except for using the electrolytic solution of Example 1-6.

Evaluation Example D-1

For each of the lithium ion secondary batteries of Examples D-1-5 and D-1-6, the voltage was adjusted to 3.65 V with a constant current at 0.5 C rate at a temperature of −10° C., and then, constant current charging was performed at 3 C rate for 10 seconds. From the current value and the amount of change in voltage before and after the charging, the direct current resistance during charging was calculated according to Ohm's law. Similarly, for each of the lithium ion secondary batteries, the voltage was adjusted to 3.65 V with a constant current at 0.5 C rate at a temperature of −10° C., and then, constant current discharging was performed at 3 C rate for two seconds. From the current value and the amount of change in voltage before and after the discharging, the direct current resistance during discharging was calculated according to Ohm's law.

Evaluation Example D-2

For each of the lithium ion secondary batteries of Examples D-1-5 and D-1-6, a charging and discharging cycle of charging up to 4.1 V with a constant current at 1 C rate at a temperature of 25° C., and pausing for 1 minute, and then, discharging down to 3.0 V with a constant current at 1 C rate, and pausing for 1 minute, was repeated by 100 cycles. The capacity retention rate was calculated by the following formula.

Capacity retention rate (%)=100×(discharge capacity at 100-th cycle)/(discharge capacity at first cycle)

Table 11 shows the results of Evaluation Example D-1 and Evaluation Example D-2.

TABLE 11

|  | Electrolytic solution | Direct current resistance during charging (Ω) | Direct current resistance during discharging (Ω) | Capacity retention rate (%) |
|---|---|---|---|---|
| Example D-1-5 | Example 1-5 Vinylene carbonate not contained | 8.0 | 6.7 | 82 |
| Example D-1-6 | Example 1-6 Vinylene carbonate | 7.5 | 6.4 | 86 |

Electrolytic solution 1-5 and Electrolytic solution 1-6 are different from each other in terms of the presence/absence of vinylene carbonate.

The lithium ion secondary batteries of the present invention each provided with a compound having a layered rock salt structure as the positive electrode active material and provided with a graphite as the negative electrode active material were confirmed to suitably operate. In addition, from the results of both lithium ion secondary batteries, addition of vinylene carbonate to the electrolytic solution of the present invention is considered to contribute to decrease in the direct current resistance and to improvement of the capacity retention rate.

The invention claimed is:

1. A secondary battery comprising:
a positive electrode active material; and
an electrolytic solution containing a specific organic solvent at a mole ratio of 1-5 relative to a metal salt,
the specific organic solvent being selected from a linear carbonate represented by formula (1-1) below and an phosphoric ester represented by formula (1-3) below,
the specific organic solvent being contained in an amount not less than 80 vol % and not greater than 100 vol % relative to an entire amount of solvent contained in the electrolytic solution,
the metal salt being a metal salt whose cation is an alkali metal, an alkaline earth metal, or aluminum and whose anion has a chemical structure including two or three types of elements selected from boron, carbon, oxygen, a halogen, phosphorus, and arsenic, wherein
the positive electrode active material is a layered compound represented by $Li_aNi_bCo_cMn_dD_eO_f$ ($0.2 \leq a \leq 1.2$, $b+c+d+e=1$, $0 \leq b \leq 1$, $0 \leq c \leq 1$, $0 \leq d \leq 0.5$, $0 \leq e < 1$, D is at least one element selected from Li, Fe, Cr, Cu, Zn, Ca, Mg, S, Si, Na, K, Al, Zr, Ti, P, Ga, Ge, V, Mo, Nb, W, and La, and $1.7 \leq f \leq 2.1$), $Li_2MnO_3$, a metal oxide having a spinel structure, a solid solution formed from a mixture of the metal oxide having a spinel structure and the layered compound, a polyanion-based compound, a tavorite-based compound, a borate-based compound, an elemental substance sulfur, a compound that is a composite of sulfur and carbon, a metal sulfide, $V_2O_5$, $MnO_2$, nitroxide, nitronyl nitroxide, galvinoxyl, phenoxyl, $Li_2MnO_3$-$LiMO_2$ (M is selected from at least one of Co, Ni, Mn, and Fe), $Li_2CoPO_4$, $Li_2MnPO_4$, $Li_2CoPO_4F$, or $Li_2MnSiO_4$, or a positive electrode active material having a reaction potential not lower than 4.5 V when a $Li^+/Li$ electrode is used as reference:

$R^{10}OCOOR^{11}$      formula (1-1), $OP(OR^{14})(OR^{15})(OR^{16})$      formula (1-3), wherein, in formulas (1-1) and (1-3), $R^{10}$, $R^{11}$, $R^{14}$, $R^{15}$ and $R^{16}$ are each independently selected from $C_nH_aF_bCl_cBr_dI_e$ that is a linear alkyl, or $C_mH_fF_gCl_hBr_iI_j$ that includes a cyclic alkyl in a chemical structure thereof, "n" is an integer not smaller than 1 and not greater than 6, "m" is an integer not smaller than 3 and not greater than 8, and "a", "b", "c", "d", "e", "f", "g", "h", "i", and "j" are each independently an integer not smaller than 0 and satisfy $2n+1=a+b+c+d+e$ and $2m-1=f+g+h+i+j$,
wherein, in $R^{14}$, $R^{15}$ and $R^{16}$, "b" is 0 and "g" is 0.

2. The secondary battery according to claim 1, wherein the specific organic solvent is contained by not less than 90 vol % and not greater than 100 vol % relative to an entire solvent contained in the electrolytic solution.

3. The secondary battery according to claim 1, wherein $R^{10}$, $R^{11}$, $R^{14}$, $R^{15}$, and $R^{16}$ are each independently selected from $C_nH_aF_b$ that is a linear alkyl or $C_mH_fF_g$ that includes a cyclic alkyl in a chemical structure thereof, "n" is an integer not smaller than 1, "m" is an integer not smaller than 3, and "a", "b", "f", and "g" are each independently an integer not smaller than 0 and satisfy $2n+1=a+b$ and $2m-1=f+g$,
wherein, in $R^{14}$, $R^{15}$ and $R^{16}$, "b" is 0 and "g" is 0.

4. The secondary battery according to claim 1, wherein the specific organic solvent is a linear carbonate represented by the formula (1-1).

5. The secondary battery according to claim 1, wherein the chemical structure of the anion of the metal salt is any one of $XO_4$, $AsX_6$, $PX_6$, $BX_4$, or $B(C_2O_4)_2$ where X is a halogen.

6. The secondary battery according to claim 5, wherein the chemical structure of the anion of the metal salt is $PF_6$ or $BF_4$.

7. The secondary battery according to claim 6, wherein the chemical structure of the anion of the metal salt is $PF_6$, and the mole ratio 4-5.

8. The secondary battery according to claim 1, wherein the chemical structure of the anion of the metal salt is $BF_4$, and the mole ratio is 2-5.

9. The secondary battery according to claim 1, being a lithium ion secondary battery comprising:
an electrolytic solution wherein the specific organic solvent is dimethyl carbonate, the metal salt is $LiPF_6$, and the mole ratio is 4-5; and
a graphite as a negative electrode active material.

10. The secondary battery according to claim 1, wherein a current collector of a positive electrode is made from aluminum.

11. The secondary battery according to claim 1, wherein the positive electrode active material is the compound represented by $Li_aNi_bCo_cMn_dD_eO_f$ having a layered rock salt structure, where $0.2 \leq a \leq 1.2$, $b+c+d+e=1$, $0 \leq b \leq 1$, $0 \leq c \leq 1$, $0 \leq d \leq 0.5$, $0 \leq e < 1$, D is at least one element selected from Li, Fe, Cr, Cu, Zn, Ca, Mg, S, Si, Na, K, Al, Zr, Ti, P, Ga, Ge, V, Mo, Nb, W, and La, and $1.7 \leq f \leq 2.1$.

12. The secondary battery according to claim 11, wherein D is at least one element selected from Al and W.

13. The secondary battery according to claim 11, wherein
$0.9 \leq a \leq 1.2$;
$0.2 \leq b$;
$0 \leq c \leq 0.55$;
$0 \leq d \leq 0.4$; and
$0 \leq e \leq 0.3$.

14. The secondary battery according to claim 1, comprising a graphite as the negative electrode active material.

15. The secondary battery according to claim 1, wherein the electrolytic solution further contains vinylene carbonate.

16. The secondary battery according to claim 1, wherein regarding an intensity of a peak derived from the specific organic solvent in a vibrational spectroscopy spectrum of the electrolytic solution, Is>Io is satisfied when an intensity of an original peak of the specific organic solvent is represented as Io and an intensity of a peak resulting from shifting of the original peak is represented as Is.

* * * * *